US011744625B2

(12) United States Patent
O'Flaherty et al.

(10) Patent No.: US 11,744,625 B2
(45) Date of Patent: Sep. 5, 2023

(54) DYNAMIC COMPRESSION DEVICES AND PROCESSES FOR MAKING AND USING SAME

(71) Applicant: MedShape, Inc., Atlanta, GA (US)

(72) Inventors: Ryan Walter O'Flaherty, Atlanta, GA (US); Jeremy Webster Blair, Atlanta, GA (US); Donald Kenneth Griffin, II, Marietta, GA (US)

(73) Assignee: MEDSHAPE, INC., Atlanta, GA (US)

( * ) Notice: Subject to any disclaimer, the term of this patent is extended or adjusted under 35 U.S.C. 154(b) by 0 days.

(21) Appl. No.: 17/711,865

(22) Filed: Apr. 1, 2022

(65) Prior Publication Data

US 2022/0265332 A1    Aug. 25, 2022

Related U.S. Application Data

(62) Division of application No. 17/184,104, filed on Feb. 24, 2021, now Pat. No. 11,291,488.

(51) Int. Cl.
| | |
|---|---|
| *A61B 17/86* | (2006.01) |
| *A61B 17/68* | (2006.01) |
| *A61B 17/72* | (2006.01) |
| *A61B 17/56* | (2006.01) |

(52) U.S. Cl.
CPC .......... *A61B 17/864* (2013.01); *A61B 17/863* (2013.01); *A61B 17/7225* (2013.01); *A61B 17/8625* (2013.01); *A61B 17/8685* (2013.01); *A61B 2017/564* (2013.01); *A61B 2017/681* (2013.01); *A61B 2017/8655* (2013.01)

(58) Field of Classification Search
CPC .............. A61B 17/8685; A61B 17/686; A61B 17/7225; A61B 17/84; A61B 17/863; A61B 17/864; A61B 17/86; A61B 17/8625; A61B 17/8645; A61B 17/68; A61B 2017/8655; A61B 2017/681; A61B 2017/564
USPC ........................................................ 606/304
See application file for complete search history.

(56) References Cited

U.S. PATENT DOCUMENTS

| | | | |
|---|---|---|---|
| 4,175,555 A | 11/1979 | Herbert | |
| 4,537,185 A | 8/1985 | Stednitz | |
| 5,019,079 A * | 5/1991 | Ross | A61B 17/863 |
| | | | 411/389 |
| 5,964,768 A | 10/1999 | Heubner | |
| 6,001,101 A | 12/1999 | Augagneur et al. | |
| 6,048,344 A | 4/2000 | Schenk | |
| 6,306,140 B1 | 10/2001 | Siddiqui | |
| 7,708,738 B2 | 5/2010 | Fourcault et al. | |
| 7,731,738 B2 | 6/2010 | Jackson et al. | |
| 7,794,483 B2 | 9/2010 | Capanni | |
| 8,267,975 B2 | 9/2012 | Mccombs et al. | |

(Continued)

*Primary Examiner* — Marcela I. Shirsat
(74) *Attorney, Agent, or Firm* — Husch Blackwell LLP; Bryan D. Stewart

(57) ABSTRACT

A compression device may include, but is not limited to, a threaded body, a sliding element, and a compression element connecting the threaded body and the sliding element. According to one embodiment, upon implantation, the threaded body contacts a first bony fragment and the sliding element contacts to a second bony fragment. In at least one embodiment, upon being engaged, the compression element applies sustained tension to the sliding element and opposing tension to the threaded body, thereby compressing the first bony fragment and the second bony fragment along a plane of contact promoting healing.

7 Claims, 18 Drawing Sheets

(56) References Cited

U.S. PATENT DOCUMENTS

| | | | |
|---|---|---|---|
| D693,929 S | 11/2013 | Fagan | |
| 8,623,060 B2 * | 1/2014 | Vlahos | A61B 17/8625 |
| | | | 606/270 |
| 8,702,768 B2 | 4/2014 | Tipirneni | |
| 9,011,505 B2 | 4/2015 | Prandi et al. | |
| 9,113,976 B2 | 4/2015 | Yevmenenko et al. | |
| D775,351 S | 12/2016 | Agarwal | |
| 9,861,413 B2 | 1/2018 | Palmer et al. | |
| D810,933 S | 2/2018 | Chrisman | |
| D939,704 S | 12/2021 | Bales | |
| 11,291,488 B1 | 4/2022 | Oflaherty | |
| 2006/0084980 A1 * | 4/2006 | Melkent | A61B 17/7007 |
| | | | 606/301 |
| 2006/0173461 A1 | 8/2006 | Kay et al. | |
| 2006/0264954 A1 | 11/2006 | Sweeney, II et al. | |
| 2007/0260248 A1 | 11/2007 | Tipirneni et al. | |
| 2007/0270855 A1 * | 11/2007 | Partin | A61B 17/7225 |
| | | | 606/279 |
| 2008/0147126 A1 | 6/2008 | Tipirneni et al. | |
| 2008/0147127 A1 | 6/2008 | Tipirneni et al. | |
| 2009/0105768 A1 | 4/2009 | Cragg | |
| 2009/0157123 A1 | 6/2009 | Appenzeller et al. | |
| 2010/0076498 A1 | 3/2010 | Tyber et al. | |
| 2012/0316607 A1 | 12/2012 | Frenk | |
| 2017/0196608 A1 | 7/2017 | Castaneda et al. | |
| 2017/0360489 A1 | 12/2017 | Palmer et al. | |
| 2018/0092677 A1 | 4/2018 | Peterson et al. | |
| 2019/0133657 A1 | 5/2019 | Orbay et al. | |
| 2022/0280197 A1 | 9/2022 | Blair | |

* cited by examiner

DYNAMIC COMPRESSION DEVICES AND PROCESSES FOR MAKING AND USING SAME

CROSS REFERENCE TO RELATED APPLICATIONS

This application is a divisional of U.S. application Ser. No. 17/184,104, filed Feb. 24, 2021, entitled "DYNAMIC COMPRESSION DEVICES AND PROCESSES FOR MAKING AND USING SAME," the disclosure of which is incorporated herein by reference in its entirety.

BACKGROUND

Injuries such as fractures may be treated, in part, using continuous compression at the fracture. Compression typically involves compressing two or more bony fragments together to promote ossification and/or resettlement processes and heal the two or more bony fragments. Previous approaches include a threaded compression device that is inserted into and compresses together two or more bony fragments. In such approaches, compressive forces are typically generated by threaded elements extending along at least a portion of the compression device (e.g., for example, at either end of the device). However, these previous approaches typically suffer compression performance issues, such as insufficient or discontinuous compression. As one example, a surgeon inserts a threaded compression device into two bony fragments, thereby generating a compressive force at a fracture site therebetween. Continuing the example, in response to the compressive force, the two bony fragments resettle and undergo resorption, thereby substantially reducing or fully dissipating the static compressive force. In this example, the inability of the threaded compression device to adapt to changes at the insertion site and provide a dynamic compressive force may result in insufficient healing at the fracture site (e.g., potentially requiring revision surgery, additional physical therapy, assistive devices, etc.).

Therefore, there is a long-felt but unresolved need for a dynamic compression device that allows for dynamic generation of sustained compressive forces between bony fragments.

BRIEF SUMMARY OF THE DISCLOSURE

Briefly described, and according to one embodiment, aspects of the present disclosure generally relate to devices and assemblies for dynamic generation of sustained compression between bony structures, as well as processes for making and using the same.

According to one embodiment, a compression device provides sustained compression to a target site by maintaining a predetermined level of tension between a first device portion affixed to a first bony fragment and a second device portion affixed to a second bony fragment. In various embodiments, the compression device compresses the first bony fragment and second bony fragment to stimulate bone resorption along one or more planes of contact and, thereby, promote healing of the bony fragments. In one or more embodiments, a compression device includes, but is not limited to, a threaded body, a sliding element, and a compression element connecting the threaded body and the sliding element. According to one embodiment, upon implantation, the threaded body is affixed to a first bony fragment and the sliding element is affixed to a second bony fragment. In at least one embodiment, upon being engaged, the compression element applies sustained tension to the sliding element and opposing tension to the threaded body, thereby compressing the first bony fragment and the second bony fragment along a plane of contact. In one or more embodiments, in contrast to previous solutions, the continuous tension of the sliding element generates substantially sustained compression at the plane of contact, which may be sustained even with resorption and/or resettling of the first and second bony fragments.

In some embodiments, the compression element is stretched prior to insertion of the compression device to a target site. For example, prior to insertion, the threaded body is pushed away from the sliding element, thereby stretching a compression element connected therebetween. In this example, to maintain the stretched state of the compression element, an insertion tool connects to the sliding element and opposes movement of the threaded body toward the sliding element. Continuing with this example, the compression device is inserted into a target site and the insertion tool is disconnected from the sliding element, thereby allowing for movement of the threaded body toward the sliding element in response to the contraction of the compression element from the stretched state.

In at least one embodiment, the compression element stretches during insertion of the compression device to a target site. In one example, the compression device rotates to penetrate into and secure to a target site. In this example, as the compression device rotates into the target site, the compression element stretches and, thereby, generates a tensile load for applying compressive forces at the target site. In some embodiments, the compression element stretches following insertion of the compression device to a target site. In one example, following insertion of the compression device to a target site, a tool couples to the compression device and reconfigures the compression element to a desired stretched state.

In various embodiments, the compression device includes one or more penetrating features (e.g., self-tapping threads, etc.) that allow the compression device to be rotated into a target site (e.g., bony material). In one example, a threaded body and a sliding element each include penetrating features that interface with and secure the compression device into bone. In this example, a compression element is connected, on opposing ends, to a first end of the threaded body and a first end of the sliding element in a manner such that the compression element is stretched a particular distance and prevented from contracting, prior to insertion into a patient. In the same example, a second end of the threaded body is inserted into a target site such that the sliding element is secured into a first bony fragment and the threaded body is secured into a second bony fragment. Continuing the example, the compression element is allowed to contract, thereby applying opposing tensile forces to the sliding element and threaded body. In the same example, the penetration features translate the tensile forces into a compressive force that compresses the first and second bony fragments toward each other.

In at least one embodiment, the threaded body and the sliding element include one or more materials including, but not limited to, titanium, titanium alloys, and other suitable materials. According to one embodiment, the threaded body includes a resilient material, such as titanium, which allows for walls of the threaded body to be thinner and lighter than would be achievable with previous device materials such as stainless steel, thereby advantageously reducing a material cost and weight of the compression device. In one or more embodiments, the compression element includes a superelastic material, such as nitinol, that allows the compression element to be stretched a pre-determined length and the resultant tension to be used to provide continuous and sustained compression of bony fragments. In one or more embodiments, the compression device is substantially formed of one or more superelastic materials. In one example, the compression device is substantially formed of nitinol material.

According to one embodiment, the threaded body and the sliding element are cannulated such that they may receive and be internally connected to a compression element on either end thereof. In one or more embodiments, the compression element is cannulated to a predetermined diameter such that the compression device may be inserted along a guidewire (e.g., by threading the guidewire through the cannulated regions of the sliding element, compression device, and threaded body). In at least one embodiment, the cannulation of the compression element is advantageous over previous approaches where the use of a centrally-disposed, but non-cannulated compression element may prohibit the use of the centrally disposed guidewire.

In some embodiments, the compression element is not cannulated. In one example, the compression element is non-cannulated and located off-center from a central axis that runs the length of the threaded body and sliding element (e.g., that are cannulated to receive a guidewire). In another example, the compression element is non-cannulated and is substantially centered on a central axis (e.g., and the compression device receives a guidewire off-center from the central axis or a guidewire is not used).

In some embodiments, the cannulation of the compression element allows for pre-configuration of potential compression levels by providing a particular degree of cannulation. In various embodiment, because the cannulation of the compression element and a maximum compression provided thereby may be inversely proportional, the level of potential compression responses of the compression element may be increased or decreased based on decreasing or increasing a diameter of the cannulation. According to one embodiment, the cannulation allows for the compression performance of the compression element to be configured without changing a footprint of the compression element. In one or more embodiments, variation of compression performance is achieved by selective laser modification (e.g., to remove material), braided material structures, and other techniques for adjusting a cross-section of the compression element. In at least one embodiment, the preservation of the compression element footprint allows for the preservation of the footprints of other compression device elements (e.g., thickness of the threaded body wall(s)) despite changing levels of compression.

In one example, a threaded body includes a particular cannulation that allows for receipt of a compression element, but also maintains a sufficient rigidity in the threaded body. In the same example, an increase in the footprint of the compression element may require a greater cannulation of the threaded body that may compromise the rigidity thereof. In an alternate example, an increase in the cannulation of the compression element may not cause an increase in the footprint thereof and thus may not require a change in the threaded body cannulation, thereby preserving the desired rigidity.

In various embodiments, the present technology allows for precise and accurate configuration of varying compression levels without modifying a footprint of the compression device or compression element. In at least one embodiment, the present compression devices and assemblies may be pre-stretched during a manufacturing or assembly process according to desired implementation parameters. In one example, a compression device is connected to an insertion tool and configured within a stretching mechanism such that a sliding element is secured in place and the threaded body can translate away from the stationary sliding element. In the same example, the stretching mechanism applies a force to the threaded body such that the threaded body is translated away from the sliding element, thereby stretching the compression element and loading a compressive force into the compression device. Continuing the example, a connection bolt is inserted through the insertion tool and secured into the sliding element such that the compression element is prevented from retracting (e.g., thereby maintaining the loaded compressive force until the connection bolt is removed).

In another example, stretching the compression element includes pulling the connected threaded body and sliding element in opposite directions to stretch the compression element and preventing retraction of the threaded body and sliding element to preserve the stretched state. In this example, the retraction of the threaded body and sliding element is temporarily opposed via one or more mechanisms including, but not limited to, pins, barriers, and releasable fittings (e.g., threaded connections, luer locks, etc.) that prevent movement of the sliding element relative to the threaded body, or vice versa. In another example, prior to or during insertion of the compression device, the compression element stretches to a predetermined level (e.g., via a stretching mechanism or as a result of the insertion) and a barrier prevents the compression element from contracting toward a pre-stretched state. In this example, the barrier is removed or automatically degrades to allow the compression element to retract from the pre-stretched state and, thereby, generate compressive forces.

In various embodiments, the compression device includes one or more mechanisms for precisely and accurately stretching the compression element, thereby providing a controlled pre-tensioning of the compression element and, thus, an accurate configuration of a desired compression performance. In one or more embodiments, the one or more mechanisms include a connection bolt and an insertion tool. In one or more embodiments, the insertion tool includes a plurality of pins that are inserted through voids in the sliding element such that the plurality of pins contact an end of the threaded body (e.g., the sliding element and threaded body being connected at either end of the compression element). According to one embodiment, the insertion tool is cannulated such that the connection bolt may be received through and freely rotate within the insertion tool. In at least one embodiment, a length of the connection bolt is greater than a length of the insertion tool such that, upon insertion, the connection bolt extends through a first end of the insertion tool and a second end of the insertion tool. In one or more embodiments, the connection bolt and sliding element include corresponding threads such that a secure, threaded connection is formed as the connection bolt is inserted through the insertion tool and rotated into the sliding element.

In various embodiments, stretching the compression element includes, but is not limited to, inserting the insertion tool into the sliding element such that the plurality of pins contact the threaded body, securing the compression device and insertion tool into a stretching device such that the sliding element is prevented from moving, and applying a force to the insertion tool that causes the plurality of pins to push the threaded body away from the sliding element, thereby stretching the compression element. According to one embodiment, following stretching of the compression element, the connection bolt is inserted through the insertion tool and securely connected to the sliding element such that the connection bolt opposes tensile forces generated by the compression element in response to stretching. In one or more embodiments, the connection bolt preserves the stretched state of the compression element as the compression device is inserted to a target site. In at least one embodiment, following insertion of the compression device into two or more bony fragments, the connection bolt is disconnected from the sliding element, thereby causing the compression element to apply tensile forces to the sliding element and threaded body, and resulting in compression of the two or more bony fragments.

According to a first aspect, a compression device assembly including: A) an elongate threaded body including: 1) a threaded body first end including one or more threaded body threads for affixing the threaded body to a first bony fragment of a patient and defining a hollow interior of the threaded body; 2) a threaded body second end including an opening to the hollow interior of the threaded body; B) a sliding element for contacting a second bony fragment of the patient, defining a hollow interior, and including a sliding element first end including an elongated portion shaped to interface with the opening of the threaded body second end; and C) a compression element operatively connected to the threaded body and the sliding element, wherein: 1) the compression element includes nitinol; and 2) the compression device assembly is configured for applying compression to the first bony fragment and the second bony fragment via the compression element.

According to a second aspect, the compression device assembly of the first aspect or any other aspect, wherein: A) the compression element is cannulated; and B) the compression device is further configured for receiving a guidewire through the cannulated compression element.

According to a third aspect, the compression device assembly of the second aspect or any other aspect, wherein: A) the compression element is in a deformed state prior to insertion into the patient; and B) applying compression to the first bony fragment and the second bony fragment via the compression element includes the compression element returning to a relaxed state from the deformed state.

According to a fourth aspect, the compression device assembly of the third aspect or any other aspect, wherein the sliding element includes a sliding element second end defining one or more pin openings for receiving one or more pins of an insertion tool.

According to a fifth aspect, the compression device assembly of the fourth aspect or any other aspect, wherein the insertion tool includes one or more pins for being received by the one or more pin openings of the sliding element.

According to a sixth aspect, the compression device assembly of the fifth aspect or any other aspect, wherein the sliding element elongated portion includes one or more pin slots for receiving the one or more pins of the insertion tool.

According to a seventh aspect, the compression device assembly of the sixth aspect or any other aspect, wherein a length of the one or more pin slots controls a maximum deformation distance of the compression device assembly.

According to an eighth aspect, the compression device assembly of the sixth aspect or any other aspect, wherein the insertion tool defines a hollow interior.

According to a ninth aspect, the compression device assembly of the eighth aspect or any other aspect, wherein the insertion tool is configured to receive a connection bolt through the insertion tool hollow interior.

According to a tenth aspect, the compression device assembly of the ninth aspect or any other aspect, wherein the sliding element includes one or more connection bolt threads for connecting the sliding element to the connection bolt.

According to an eleventh aspect, the compression device assembly of the tenth aspect or any other aspect, wherein the connection bolt passes through the insertion tool hollow interior and attaches to the one or more connection bolt threads of the sliding element for holding the sliding element in position with the compression element in the deformed state.

According to a twelfth aspect, the compression device assembly of the eleventh aspect or any other aspect, wherein the connection bolt includes: A) a first end for connection to the sliding element; and B) a second end, opposite the first end, that is configured to prevent a full length of the connection bolt passing through the insertion tool hollow interior.

According to a thirteenth aspect, the compression device assembly of the eleventh aspect or any other aspect, wherein compression device assembly is configured for receiving the guidewire through the hollow interior of threaded body, the cannulated compression element, and the hollow interior of the sliding element, the hollow interior of the insertion tool, and through a hollow interior of the connection bolt for guiding the compression device assembly to a particular location in the patient.

According to a fourteenth aspect, the compression device assembly of the thirteenth aspect or any other aspect, wherein, upon removing the connection bolt, the compression device assembly applies compression to the first bony fragment and the second bony fragment via the compression element returning to the relaxed state from the deformed state.

According to a fifteenth aspect, the compression device assembly of the fourteenth aspect or any other aspect, wherein the compression device assembly is configured such that the insertion tool is removable once the connection bolt is removed. According to a sixteenth aspect, the compression device assembly of the fifteenth aspect or any other aspect, wherein the compression element is operatively connected to the threaded body and the sliding element via threads.

According to a seventeenth aspect, the compression device assembly of the sixteenth aspect or any other aspect, wherein a perimeter of the opening of the threaded body second end includes a hexagonal shape.

According to an eighteenth aspect, the compression device assembly of the sixteenth aspect or any other aspect, wherein: A) a set of threads connecting the sliding element and the compression element includes a first thread direction; B) and a second set of threads connecting the threaded body and the compression element includes a second thread direction that is opposite the first thread direction.

According to a nineteenth aspect, a method including: A) inserting a compression device assembly into a patient, wherein the compression device assembly includes: 1) an elongate threaded body including: i) a threaded body first end defining a hollow interior of the threaded body; and ii) a threaded body second end including an opening to the hollow interior of the threaded body; 2) a sliding element defining a hollow interior and including a sliding element first end including an elongated portion shaped to interface with the opening of the threaded body second end; and 3) a nitinol compression element operatively connected to the threaded body and the sliding element; B) contacting the threaded body with a first bony fragment of the patient via one or more threaded body threads; C) contacting the sliding element with a second bony fragment of the patient; and D) applying compression to the first bony fragment and the second bony fragment via the compression element returning to a relaxed state from a deformed state.

According to a twentieth aspect, the method of the nineteenth aspect or any other aspect, wherein: A) the compression element is cannulated; B) a guidewire is further received through the cannulated compression element; and C) the method further includes guiding the compression device assembly along the guidewire to a particular location in the patient;

According to a twenty-first aspect, the method of the nineteenth aspect or any other aspect, wherein the compression element is in the deformed state prior inserting the compression device assembly into the patient.

According to a twenty-second aspect, the method of the nineteenth aspect or any other aspect, wherein the compression element is in the relaxed state prior to inserting the compression device assembly into the patient.

According to a twenty-third aspect, the method of the nineteenth aspect or any other aspect, wherein: A) the compression element includes a compression element elongated portion between a compression element first end and a compression element second end; and B) the compression element first end and the compression element second end each include a sloped region for transitioning to the compression element elongated portion.

According to a twenty-fourth aspect, the method of the nineteenth aspect or any other aspect, wherein: A) the sliding element includes one or more sliding element threads; and B) a diameter of the one or more threaded body threads is less than a diameter of the one or more sliding element threads.

According to a twenty-fifth aspect, the method of the nineteenth aspect or any other aspect, wherein the threaded body includes a wall thickness of about 0.5-4.0 mm.

According to a twenty-sixth aspect, a compression device assembly including: A) an elongate threaded body including: 1) a threaded body first end including one or more threaded body threads for affixing the threaded body to a first bony fragment of a patient and defining a hollow interior of the threaded body; and 2) a threaded body second end including a threaded body interface portion; B) a sliding element for contacting a second bony fragment of the patient, defining a hollow interior, and including a sliding element first end including a sliding element interface portion shaped to interface with the threaded body interface portion; and C) a compression element operatively connected to the threaded body and the sliding element, wherein: 1) the compression element includes nitinol; and 2) the compression device assembly is configured for applying compression to the first bony fragment and the second bony fragment via the compression element.

According to a twenty-seventh aspect, the compression device assembly of the twenty-sixth aspect or any other aspect, wherein: A) the threaded body interface portion includes a tapered portion; and B) the sliding element interface portion includes an elongated portion for inserting into the tapered portion.

According to a twenty-eighth aspect, the compression device assembly of the twenty-seventh aspect or any other aspect, wherein the tapered portion includes a perimeter with at least two corners.

According to a twenty-ninth aspect, the compression device assembly of the twenty-eighth aspect or any other aspect, wherein the tapered portion includes a hexagon-shaped perimeter.

According to a thirtieth aspect, the compression device assembly of the twenty-sixth aspect or any other aspect, wherein: A) the threaded body interface portion includes an elongated portion; and B) the sliding element interface portion includes a tapered portion for receiving the elongated portion.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
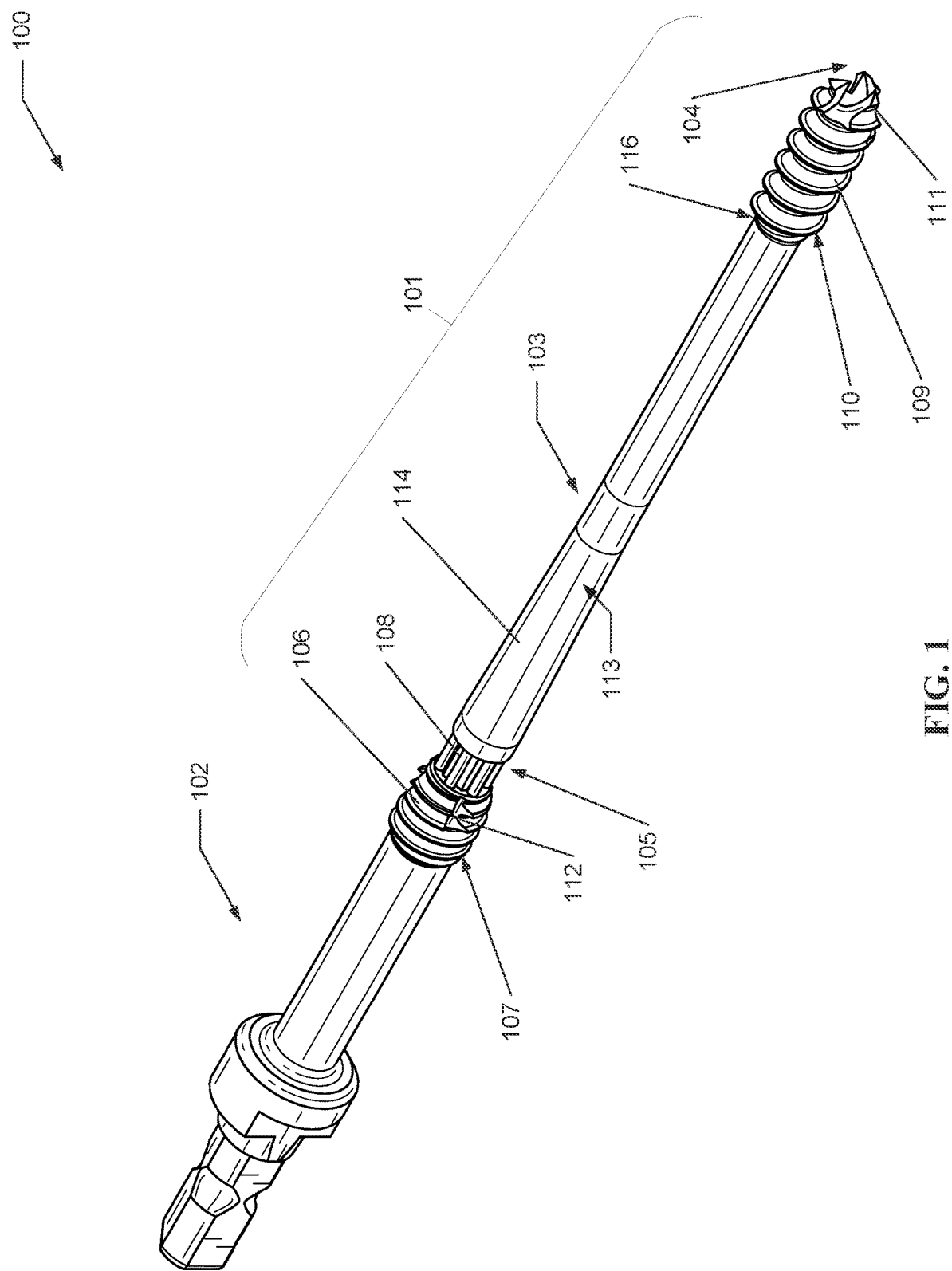
FIG. 1 shows a perspective view of an exemplary compression assembly according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to devices and assemblies for providing precise and accurate compression of bony structures, as well as processes for making and using the same.

In one or more embodiments, a compression device includes, but is not limited to, a threaded body, a sliding element, and one or more compression elements. In at least one embodiment, the threaded body is cannulated such that a portion (or, in some embodiments, a substantial length) of the compression element is sheathed by the threaded body. In one or more embodiments, the threaded body and the sliding element include internal fittings for connecting to corresponding fittings on each end of a compression element. In one example, the threaded body and the sliding element each include threads sized to receive corresponding threads of the compression element.

In at least one embodiment, the compression element provides for dynamic generation of sustained compressive forces between two or more bony fragments (e.g., along a plane of fracture through which the compression device is inserted). According to one embodiment, the compression element is cannulated according to a predetermined diameter. In at least one embodiment, the cannulation of the compression element, threaded body, and sliding element permit the compression device to be inserted along a guide wire (e.g., translated through the cannulated portions) into a target site. In at least one embodiment, the cannulation of the compression element allows for pre-configuration of varying compression levels without affecting an overall footprint of the compression element.

In various embodiments, the compression element includes a superelastic material, such as nitinol. In one or more embodiments, the threaded body, sliding element, insertion tool, connection rod, and/or connecting pins include one or more materials including, but not limited to, titanium, titanium alloys, and other materials.

Exemplary Embodiments

Referring now to the figures, for the purposes of example and explanation of the fundamental processes and components of the disclosed systems and methods, reference is made to FIG. 1, which shows a perspective view of an exemplary compression assembly 100 according to various embodiments of the present disclosure. As will be understood and appreciated, the exemplary compression assembly 100 shown in FIG. 1 represents merely one approach or embodiment of the present system, and other aspects are used according to various embodiments of the present system.

In various embodiments, the assembly 100 includes a compression device 101 and an insertion tool 102. In some embodiments, the compression device 101 and insertion tool 102 are provided separately (e.g., unattached or un-assembled), such as, for example, in a kit. According to one embodiment, the compression device 101 and insertion tool 102 are provided as shown in FIG. 1 and the compression device 101 is provided pre-stretched according to predetermined parameters. In alternate embodiments, the compression device 101 and insertion tool 102 are provided as the assembly 100, but the compression device is not pre-stretched (e.g., the pre-stretching being performed by a user, such as a technician or surgeon). In some embodiments, the compression device 101 is insertable without the insertion tool 102.

Figure 2:
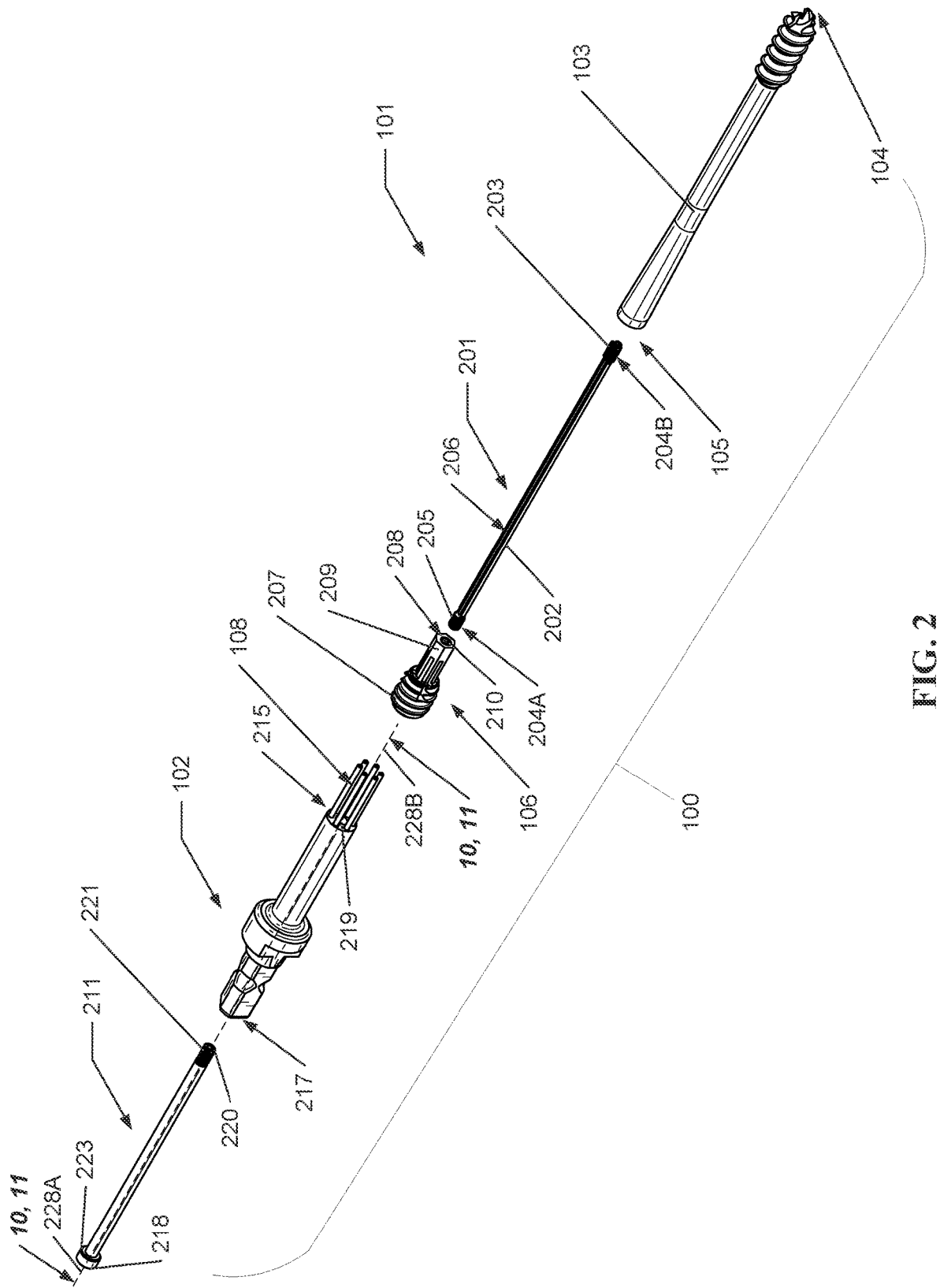
FIG. 2 shows an exploded view of an exemplary compression assembly according to one embodiment of the present disclosure.

In one or more embodiments, the compression device 101 includes a threaded body 103, a sliding element 106, and a compressive element 201 (not shown in FIG. 1, see FIG. 2). In at least one embodiment, the threaded body 103 and the sliding element 106 are configured to penetrate into biological material, such as bone, at a target site. In various embodiments, the threaded body 103 and sliding element 106 are cannulated such that they may receive the compressive element 201 and/or a guidewire (e.g., a K-wire) through the cannulated portions.

According to one embodiment, the threaded body 103 includes a first end 104 and a second end 105. In various embodiments, the threaded body 103 includes a tip 109 at the first end 104. In one or more embodiments, the threaded body 103 includes a shaft 114 between the second end 105 and a tip end 116 (e.g., end of the tip 109). In one or more embodiments, the tip 109 is integrally formed with the shaft 114. According to one embodiment, the shaft 114 and the tip 109 are connected by one or more mechanisms including, but not limited to, threaded fittings, adhesives, welds, friction fits, and other connection mechanisms.

In at least one embodiment, the tip 109 is configured to penetrate and drill into tissue, such as bone, at a target site. In one or more embodiments, the tip 109 includes threads 110 and one or more blades 111 for drilling into material, such as bone, via rotation of the compression device 101. In various embodiments, the threads 110 interface with tissue, such as bone, to secure an implanted position of the compression device 101 and resist pullout and pull-through forces experienced thereby.

In at least one embodiment, the threaded body 103 and sliding element 106 are attached to either end of the compression element 201. In one example, the threaded body 103 and sliding element 106 include inner threads configured to interface with corresponding threads of the compression element 201 (as discussed regarding FIG. 2).

Figure 3:
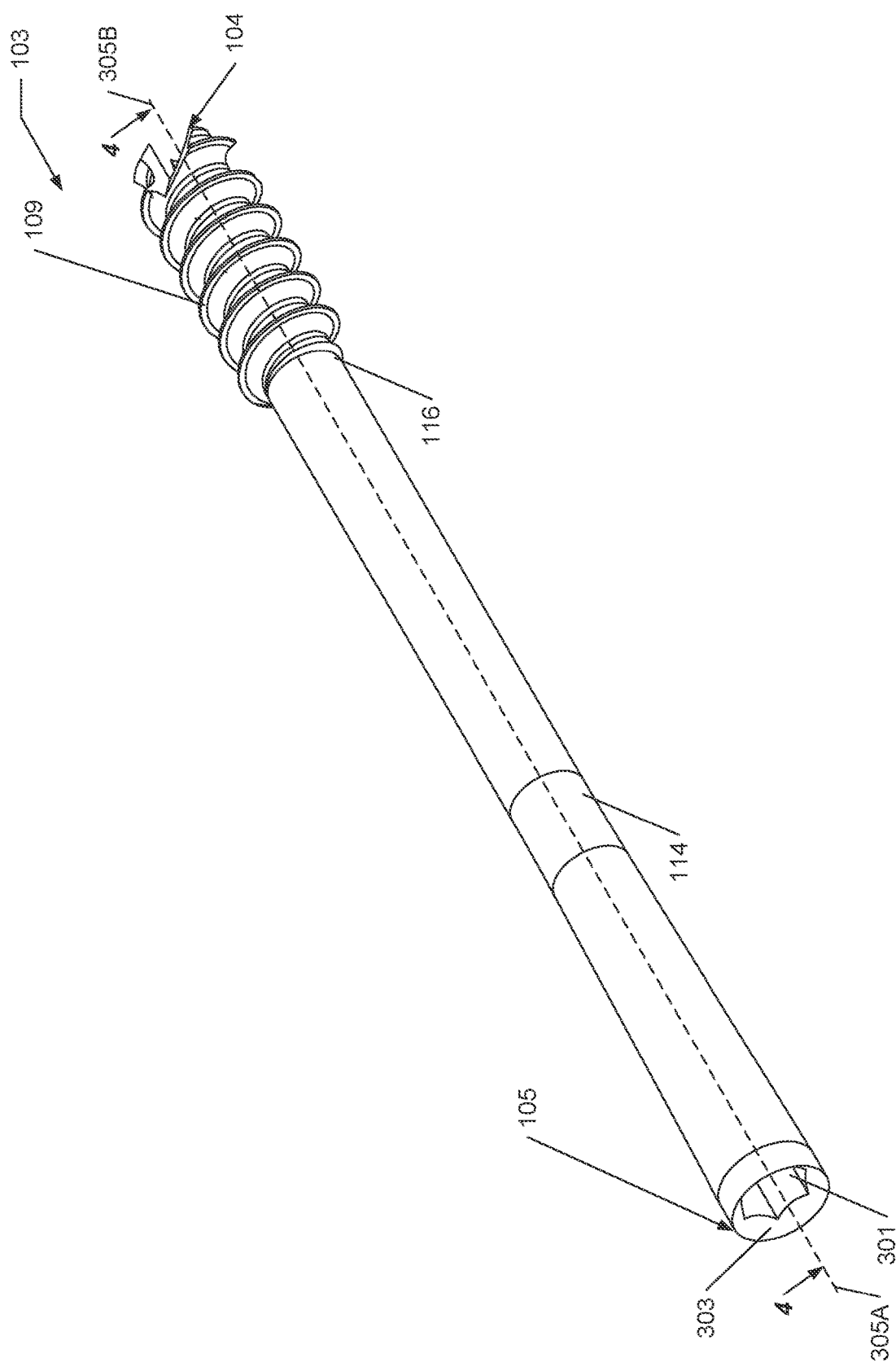
FIG. 3 shows a perspective view of an exemplary threaded body according to one embodiment of the present disclosure.

As will be understood from discussions herein, the threaded body 103 and the sliding element 106 may interface in any suitable way. According to one embodiment, at the second end 105 of the threaded body 103 is configured to receive a portion of the sliding element 106. In at least one embodiment, the second end 105 includes an opening that receives an end of the sliding element 106 (as shown in FIG. 3). According to one embodiment, the angular interface between the sliding element 106 and the second end 105 allows the sliding element 106 and threaded body 103 to be rotated in unison, for example, during insertion or extraction of the compression device 101.

According to one or more embodiments, the sliding element 106 may receive a portion of the threaded body 103. In these embodiments (and others), the threaded body 103 includes an elongated portion (not shown) that is received by the sliding element 106, such that the interface between the sliding element 106 and threaded body 103 allows the sliding element 106 and the threaded body 103 rotate in unison.

In one or more embodiments, the sliding element 106 is configured to receive a plurality of control pins 108 that extend from the insertion tool 102. In at least one embodiment, the plurality of control pins 108 are integrally formed with the insertion tool 102. In some embodiments, the plurality of pins 108 are inserted and/or attached to the insertion tool 102. In one or more embodiments, the sliding element 106 includes threads 107 for drilling into tissue, such as bone, and for securing an implanted position of the compression device 101. In various embodiments, the threads 107 resist pullout and pull-through forces experienced by the compression device 101. In at least one embodiment, the sliding element 106 includes one or more self-tapping features 112 that pierce tissue and expand an implantation site to accommodate the sliding element 106. In one embodiment, the one or more self-tapping features 112 are flutes with sharpened edges that cut threads into tissue as the compression device 101 is rotated, the formed threads being sized to interface with the threads 107 and secure the compression device 101.

In one or more embodiments, the compression device 101 is inserted through a target such that the sliding element 106 contacted or affixed to a first bony fragment and the threaded body 103 is contacted or affixed to a second bony fragment (e.g., threads 110 and threads 107 securing the position of the compression device 101). According to one embodiment, following implantation, the compression element 201 is engaged and applies a tensional force to the sliding element 106 and an opposing tensional force to the threaded body 103. In various embodiments, the opposing tensional forces compress the sliding element 106 and the threaded body 103 toward each other and, thereby, causes the threads 110 and threads 107 to compress the first bony fragment and the second bony fragment. In alternate embodiments, the sliding element 106 and/or threaded body 103 includes a shaped head including a surface oriented and extending perpendicular to the length of the compression device 101 such that the surface interfaces with or otherwise contacts surrounding tissue, thereby generating the compressive force.

In at least one embodiment, the threaded body 103 includes a generally cylindrical shape. In various embodiments, the threaded body 103 (e.g., or at least the shaft 114) tapers in diameter between the second end 105 and the tip end 116. In one or more embodiments, the threaded body 103 includes a substantially smooth surface 113 that allows the compression device 101 to translate through a target site and into biological materials, such as bone.

In one or more embodiments, the threaded body 103 and the sliding element 106 include one or more materials including, but not limited to, titanium, titanium alloys, and other materials. In some embodiments, the threaded body 103 and sliding element 106 include different materials. In one or more embodiments, the one or more materials included in the various elements of the compression device 101 are biocompatible and biologically inert.

Figure 10:
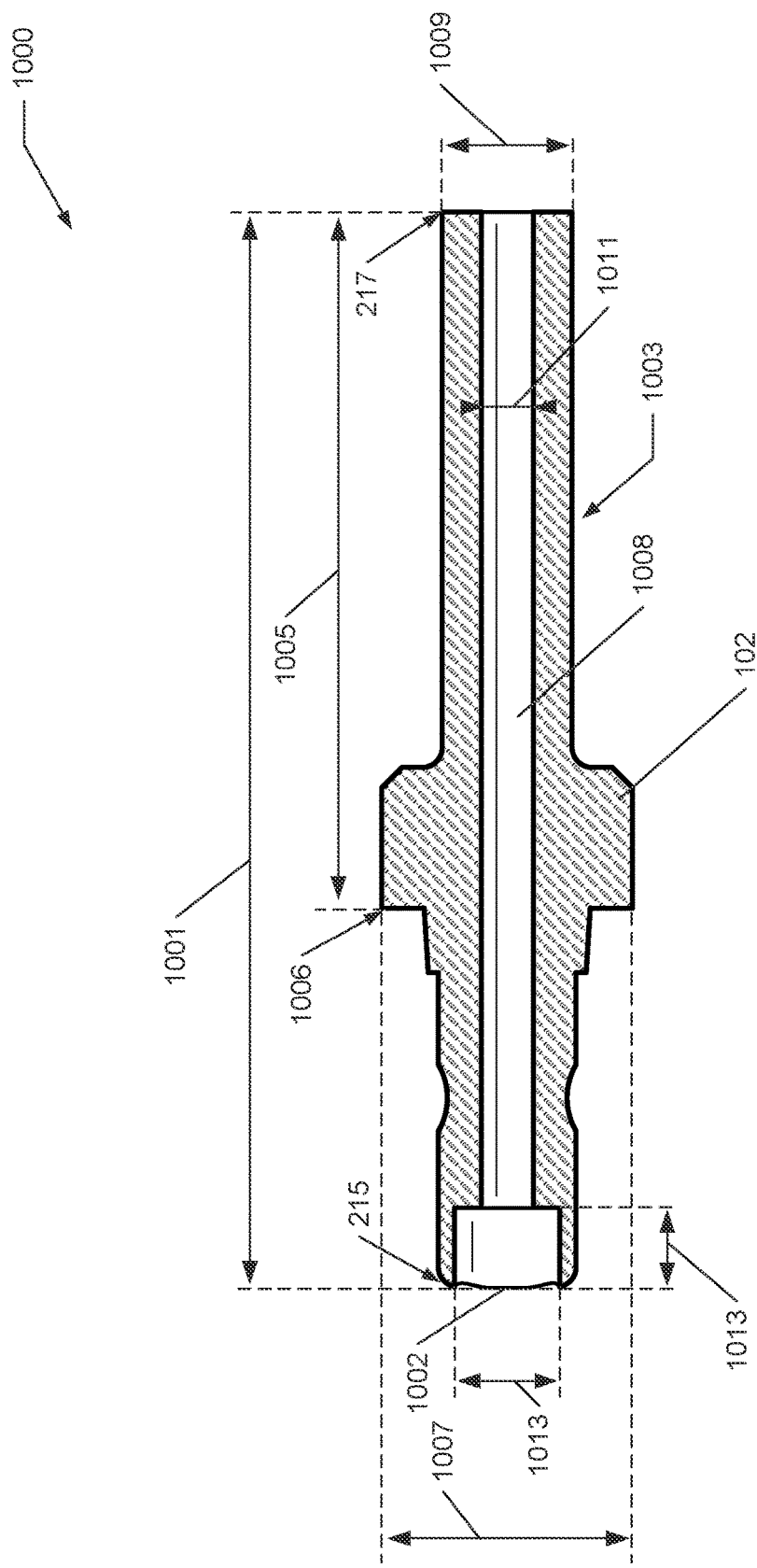
FIG. 10 shows a cross-sectional view of an exemplary insertion tool according to one embodiment of the present disclosure.
Figure 11:
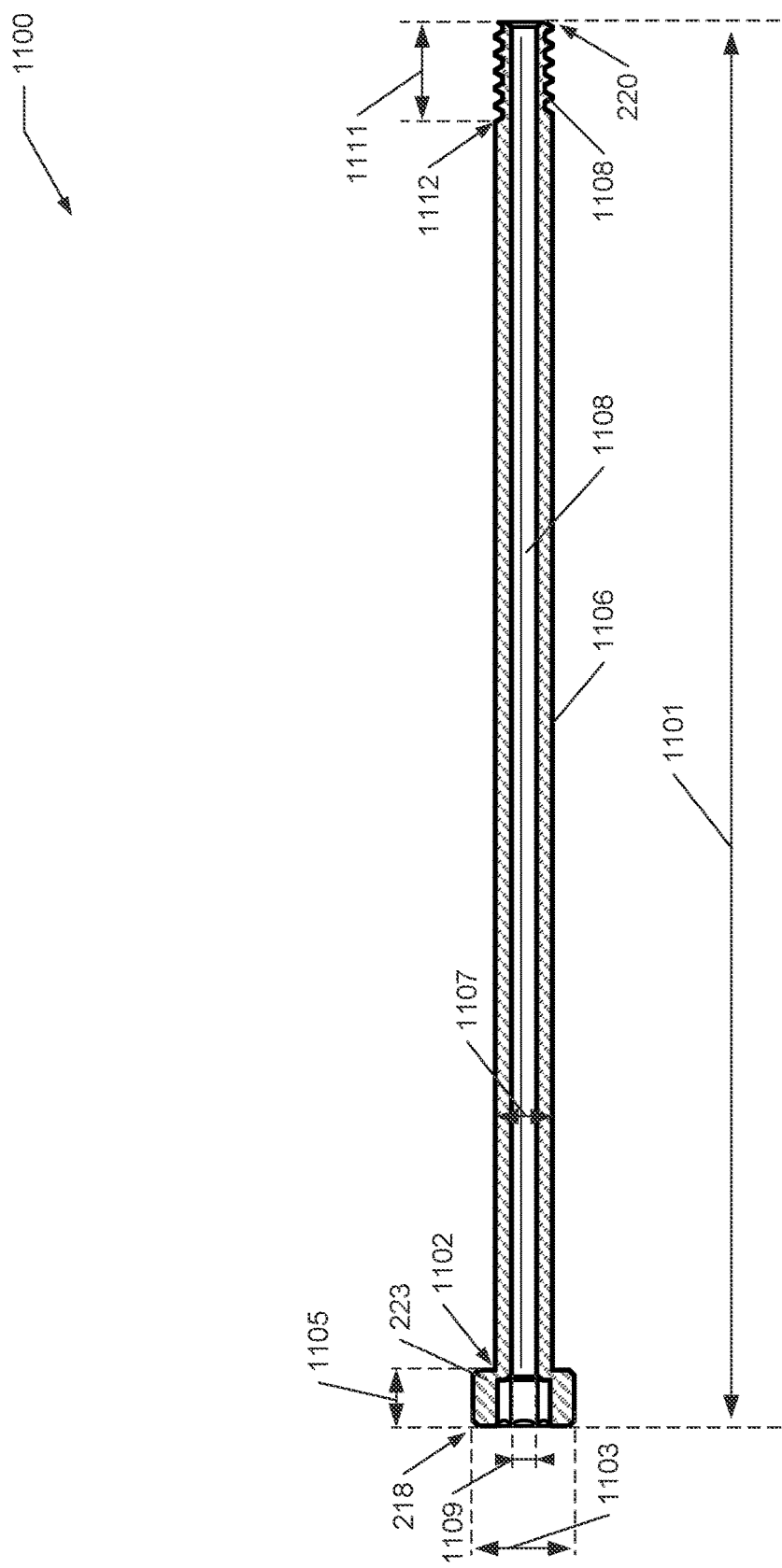
FIG. 11 shows a cross-sectional view of an exemplary connection bolt according to one embodiment of the present disclosure.

In various embodiments, a section line 228A, 228B indicates a cross section 1000 and a cross-section 1100 that are shown in FIG. 10 and FIG. 11, respectively.

FIG. 2 shows an exploded view of the assembly 100. In various embodiments, the assembly 100 includes the compression device 101, insertion tool 102, and a connection bolt 211. According to one embodiment, the compression device 101 includes the threaded body 103 configured for attachment to a first end 203 of the compression element 201, and includes the sliding element configured for attachment to a second end 205 of the compression element 201.

In various embodiments, the compression element 201 includes a generally cylindrical shape. In at least one embodiment, a cross-section of the compression element 201 includes one or more shapes, including, but not limited to, circles, ellipses, semi-circles (or other partial circles), discs, other polygons, and other shapes. According to one embodiment, the compression element 201 includes a shaft 202 that is cannulated to a predetermined diameter. In at least one embodiment, the shaft 202 includes a slot 206. In one or more embodiments, the slot 206 is formed from cannulation of the compression element 201. In various embodiments, in the assembled compression device 101, the slot 206 is open to the internal portion of the threaded body 103. In alternative embodiments, the slot 206 is absent. For example, the shaft 202 is cannulated and is fully enclosed by an exterior surface.

According to one embodiment, the first end 203 and second end 205 of the compressive element 201 includes threads 204A, 204B for interfacing with corresponding threads of the threaded body 103 and the sliding element 106. In at least one embodiment, the threads 204B and threads 204A demonstrate opposing handedness. In one example, the threads 204B are left-handed threads, and the threads 204A are right-handed threads. In one or more embodiments, the opposing handedness of the threads 204A and threads 204B allows for the compression element 201 to be connected to the threaded body 103 while remaining connected to the sliding element 106.

In various embodiments, the sliding element 106 includes a first portion 207 and a second portion 209. In one or more embodiments, the second portion 209 is shaped to fit into a receiving portion of the threaded body 103 towards at the second end 105 thereof. In at least one embodiment, the second portion 209 includes one or more shapes including, but not limited to, circles, hexalobes, hexagons, triangles, squares, and other polygons. According to one embodiment, the shape of the second portion 209 conforms to a shape of the receiving portion of the threaded body 103. In one or more embodiments, the second portion 209 includes a void 208 for receiving the second end 205 of the compression element. In various embodiments, the void 208 includes an internal portion 210 that is threaded to interface with the threads 204A and thereby secure the sliding element to the compression element 201. In alternate embodiments, the internal portion 210 includes one or more non-threaded connection mechanisms, such as, for example, a bayonet fitting.

In one or more embodiments, the connection bolt 211 is configured for maintaining the compression element 201 in a deformed state. According to one embodiment, the connection bolt 211 includes a substantially cylindrical shape. In at least one embodiment, a cross-section of the rod 211 includes one or more shapes including, but not limited to, circles, semi-circles, hexagons, and other polygons. In one or more embodiments, the connection bolt 211 includes a head 223 at a first end 218 and a connection mechanism 221 at a second end 220.

In at least one embodiment, the connection bolt 211 is inserted into the compression assembly 100 during an assembly process. In one or more embodiments, the pre-tensioning of the compression element 201 is performed according to predetermined implantation parameters, for example, a desired compression force to be applied to bony fragments of a patient. In at least one embodiment, the compression element 201 is inserted into the second portion 209 of the sliding element 106 and rotated to secure the connection via the interface of threads 204A and threads 208. In one or more embodiments, the compression element 201 and second portion 209 of the sliding element 106 are inserted into the second end 105 of the threaded body 103. In various embodiments, at the second end 105 an opening (shown as opening 301 in FIG. 3) receives the second portion 209 of the sliding element 106. According to one embodiment, the compression element 201 and threaded body 103 are connected by twisting the compression element 201 (e.g., via a tool inserted through the first end 104) and thereby causing the threads 204B and internal threads 415 (see FIG. 4) to engage and secure the connection.

In one or more embodiments, the insertion tool 102 is connected to the compression device 101 via the plurality of control pins 108 inserted into a first end 215 of the insertion tool 102 and further inserted through the voids 707 (see FIG. 7) of the sliding element 106. In various embodiments, stretching the compression element 201 includes securing a position of the sliding element 106 while applying a force to the threaded body 103 via the plurality of control pins 108. In at least one embodiment, the applied force causes the threaded body 103 to translate away from the stationary sliding element 106, thereby causing the compression element 201 to stretch. According to one embodiment, to secure the stretched/deformed state of the compression element 201, a connection bolt 211 is inserted through a second end 217 of the insertion tool 102 and further inserted into the sliding element 106. In at least one embodiment, the head 223 (which may be in the form of a nail or screw head) prevents further insertion of the connection bolt 211 into the compression assembly 100. In various embodiments, the connection bolt 211 is rotated to connect to the sliding element 106 by an interface of the threads 221 and internal threads 908 (see FIG. 9). According to one embodiment, upon being connected to the sliding element 106, the connection bolt 211 prevents the sliding element 106 from translating toward the threaded body, thereby preserving the stretched/deformed state of the compression element 201.

According to one embodiment, the connection bolt 211 is provided in a kit (e.g., including the components of the compression assembly 100) and a user inserts and rotates the connection bolt 211 to achieve a desired pre-tensioning of the compression device 101.

In one or more embodiments, a maximum stretch of the compression element 201 may be configured based on one or more factors including, but not limited to, the length of the threads 221, the length of the control pins 108, and/or the length of the insertion tool 102. In at least one embodiment, the one or more factors prevent the compression element 201 being stretched to or past a failure length (e.g., a stretch distance at which the compression element breaks or is otherwise rendered dysfunctional). In one example, a length of the control pins 108 is such that a maximum stretch length of the compression element 201 is less than a failure stretch length of the material thereof. In another example, a kit including the compression assembly 100 includes multiple sets of control pins 108, each set having control pins 108 of a particular length, thereby providing a user with various options for the magnitude of compression provided by the compression device 101.

In at least one embodiment, the control pins 108 include a sequence of visible markings that are revealed as the sliding element 106 is progressively drawn upwards during pre-stretching. In one or more embodiments, as revealed, each visible marking indicates the magnitude of compression being provided by the current stretch length of the compressive element 201. In one example, the sequence of visible markings include compression magnitudes. In another example, the sequence of visible markings include stretch length magnitudes corresponding to the stretch length of the compression element 201. In another example, the sequence of visible markings includes a failure point marker, such as a red line, that indicates a maximum stretch length of the compression element 201 before failure or other dysfunction may occur.

FIG. 3 shows a perspective view of the threaded body 103. In one or more embodiments, the threaded body 103 includes one or more materials including, but not limited to, titanium, stainless steel, and other materials. In at least one embodiment, the threaded body 103 includes titanium that allows the threaded body 103 to demonstrate desired rigidity while maintaining a sufficiently small footprint.

According to one embodiment, the threaded body 103 includes an opening 301 shaped to receive the second portion 209 of the sliding element 106 (see FIG. 2). In at least one embodiment, the opening 301 is shaped to conform to a footprint of the second portion 209 of the sliding element 106. In one example, the second portion 209 of the sliding element 106 includes a hexagonal footprint and the opening 301 includes a hexagonal shape sized to conform to the hexagonal footprint. In various embodiments, the shape of the opening 301 includes, but is not limited to, hexalobe, circle, square, hexagon, and other polygons. In one or more embodiments, a sloped region 303 transitions the second end 105 to the opening 301. It will be understood and appreciated that one or more slopes of varying degree and/or arrangement may transition the second end 105 to the opening 301. In some embodiments, the second end 105 transitions to the opening 301 without a slope. In various embodiments, a section line 305A, 305B indicates a cross-section 400 of the threaded body 103 that is shown in FIG. 4.

Figure 4:
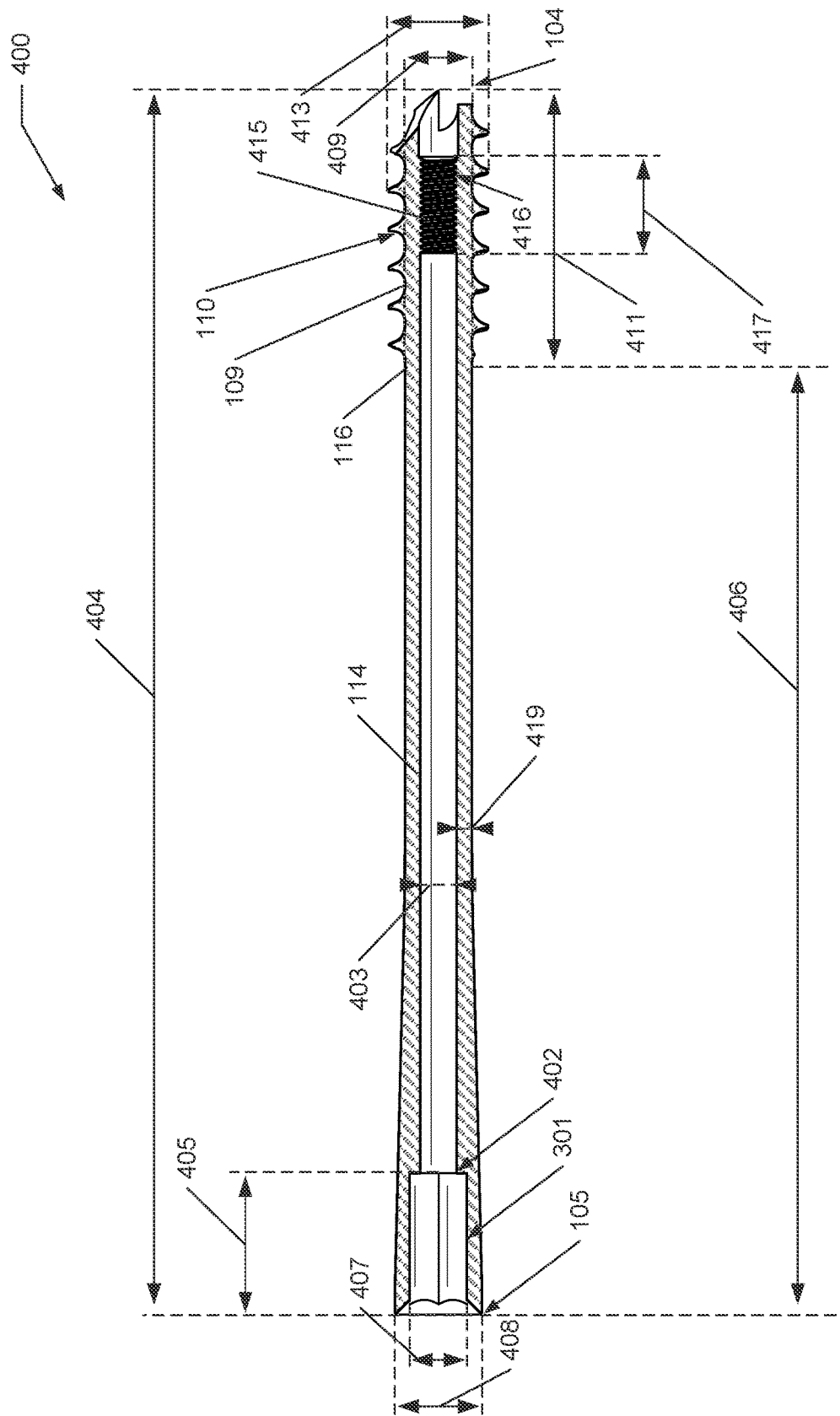
FIG. 4 shows a cross-sectional view of an exemplary threaded body according to one embodiment of the present disclosure.

FIG. 4 shows a cross-section 400 of the threaded body 103. In one or more embodiments, the threaded body 103 includes a length 404 between the second end 105 and first end 104. According to one embodiment, the length 404 measures about 20-160 mm, about 20-40 mm, about 40-60 mm, about 60-80 mm, about 80-100 mm, about 100-120 mm, about 120-140 mm, or about 140-160 mm. In one or more embodiments, the shaft 114 includes a length 406 between the second end 105 and the tip end 116. In at least one embodiment, the length 406 measures about 40-80 mm, about 40-50 mm, about 50-60 mm, about 60-70 mm, about 67 mm, or about 70-80 mm.

In one or more embodiments, the threaded body 103 is cannulated between the first end 104 and the second end 105. According to one embodiment, between the first end 105 and an end 402, the threaded body 103 includes a diameter 403 that measures about 1.0-4.0 mm, about 1.0-1.5 mm, about 1.5-2.0 mm, about 2.0-2.5 mm, about 2.6 mm, about 2.5-3.0 mm, about 3.0-3.5 mm, or about 3.5-4.0 mm. In at least one embodiment, the diameter 403 provides sufficient rigidity in the threaded body 103 and permits passage of the compression element 201 through the threaded body 103.

In one or more embodiments, the opening 301 includes a length 405 between the second end 105 and the end 402. In at least one embodiment, the length 405 measures about 5-15 mm, about 5-7 mm, about 7-9 mm, about 9-11 mm, about 10 mm, about 11-13 mm, or about 13-15 mm. In various embodiments, the opening 301 includes a width 407. According to one embodiment, the width 407 measures about 3.0-6.0 mm, about 3.0-4.0 mm, about 4.0-5.0 mm, about 4.68 mm, or about 5.0-6.0 mm. In at least one embodiment, the width 407 is based on a footprint of the second portion 209 of the sliding element 106 (e.g., as shown in FIG. 2).

In one or more embodiments, the shaft 114 includes a diameter 408 that measures about 4.0-8.0 mm, about 4.0-5.0 mm, about 5.0-6.0 mm, about 6.0-7.0 mm, about 6.15 mm, or about 7.0-8.0 mm. In various embodiments, the shaft 114 tapers from the diameter 408 at the second end 105 to a second diameter 409 toward the first end 104. According to one embodiment, the second diameter 409 measures about 3.0-6.0 mm, about 3.0-4.0 mm, about 4.0-5.0 mm, about 4.75 mm, or about 5.0-6.0 mm. In some embodiments, the diameter of the shaft 114 is substantially constant (e.g., equal to a substantially constant diameter 408 or diameter 409).

In one or more embodiments, the tip 109 includes a length 411 between the tip end 116 and the first end 104. According to one embodiment, the length 411 measures about 17.0-22.0 mm, about 17.0-18.0 mm, about 18.0-19.0 mm, about 19.0-20.0 mm, about 19.271 mm, about 20.0-21.0 mm, or about 21.0-22.0 mm. In various embodiments, the tip 109 includes a diameter 413 that measures about 5.0-9.0 mm, about 5.0-6.0 mm, about 6.0-7.0 mm, about 7.0 mm, about 7.0-8.0 mm, or about 8.0-9.0 mm. In at least one embodiment, the diameter 413 is based on a height of the threads 110 as measured, for example, from the surface 113 of the shaft 114. In one or more embodiments, the diameter 413 is based on a desired bore size for inserting the compression device 101 into a target site.

In various embodiments, the threaded body 103 includes an internal portion 415 that includes one or more connection mechanisms for connecting a compression element 201 to the threaded body 103. In at least one embodiment, the internal portion 415 includes threading 416 configured to interface with threads 204B (FIG. 2) and secure a compression element 201 to the threaded body 103. In alternate embodiments, the internal portion includes one or more connection mechanisms, such as, for example, a bayonet fitting or other suitable mechanisms. According to one embodiment, the internal portion 415 includes a length 417 that measures about 5.0-15.0 mm, about 5.0-7.0 mm, about 7.0-9.0 mm, about 9.0-11.0 mm, about 10.0 mm, about 11.0-13.0 mm, or about 13.0 mm-15.0 mm.

In various embodiments, the threaded body 103 includes a wall thickness 419. As will be understood from discussions herein, the wall thickness 419 may vary along a length of the threaded body 103. In one or more embodiments, the wall thickness 419 measures about 0.5-4.0 mm, about 0.5-1.0 mm, about 1.0-1.5 mm, about 1.25 mm, about 1.5-2.0 mm, about 2.15 mm, about 2.0-2.5 mm, about 2.5-3.0 mm, about 3.0-3.5 mm, about 3.5-4.0 mm, or about 4.0-4.5 mm. In at least one embodiment, the wall thickness 419 maintains sufficient levels of rigidity in the threaded body 103 and permits passage of the compression element 201 through the threaded body 103. According to one embodiment, the wall thickness 419 varies between about 0.5-2.0 mm between the first end 104 and the second end 105. In one example, the wall thickness 419 measures about 0.5 mm at the second end 105 and about 1.25 mm at the end 402. In at least one embodiment, the threaded body 103 may include an average wall thickness of about 1.25 mm.

Figure 5:
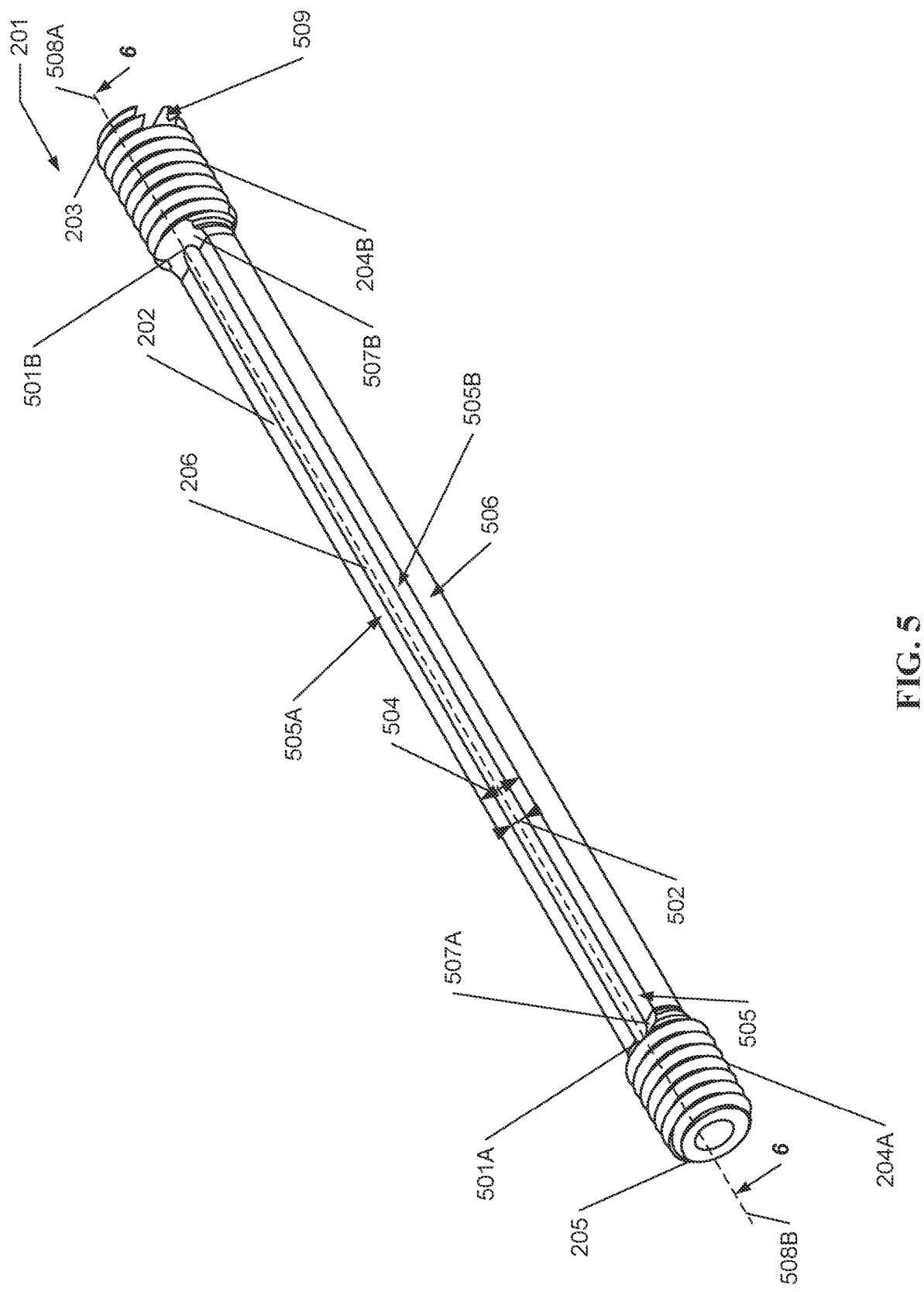
FIG. 5 shows a perspective view of an exemplary compression element according to one embodiment of the present disclosure.

FIG. 5 shows a perspective view of the compression element 201. In one or more embodiments, the shaft 202 and slot 206 thereof are located between a first end 501A and a second end 501B. In one or more embodiments, the slot 206 includes a width 502 that measures about 1.0-3.0 mm, about 1.0-1.5 mm, about 1.5-2.0 mm, about 1.88 mm, about 2.0-2.5 mm, or about 2.5-3.0 mm. In at least one embodiment, the width 502 provides a particular level of cannulation in the shaft 202, such as, for example, a cannulation level sufficient for passing a guidewire through the shaft 202.

In at least one embodiment, a shape of the shaft 202 includes a generally flat top surface 505A, 505B spaced opposite from a generally flat or rounded bottom surface (not shown). In one or more embodiments, a first convex surface 506 and an oppositely-oriented second convex surface (not shown) connect to and bridge corresponding edges of the top surface 505A, 505B and bottom surface. In at least one embodiment, a cross-section of the shaft 202 (e.g., taken perpendicular to the section line 508A, 508B) includes two generally trapezoidal shapes in which a longest side of each shape includes a convex curve.

In one or more embodiments, at each end 501A, 501B, the shaft 202 includes sloped portions 507A, 507B that transition the shaft 202 to the second end 205 and first end 203, respectively. In at least one embodiment, the sloped portions advantageously reduce stress concentrations as compared to other connections or transitions, such as corners.

In various embodiments, the compression element 201 forms a notch 209 near the first end 203 that is shaped to receive a tool for connecting the compression element 201 to the threaded body 103. In one example, the notch 509 includes a predetermined depth that allows the notch 509 to receive and engage with a tool for rotating the compression element 201. In one example, the notch 509 is configured to receive a flathead screw driver inserted through a first end 104 (see. FIG. 1) of the threaded body 103 for rotating the compression element 201 within the threaded body 103 and engaging threaded connections therebetween.

In one or more embodiments, the compression element 201 is cannulated to a predetermined diameter. In at least one embodiment, the cannulation of the compression element 201 allows for the insertion of the compression element 201 along a guidewire, such as a K-wire, received through the cannulation. In various embodiments, the cannulation diameter may determine a maximum compressive force provided by the compression element 201. According to one embodiment, the degree of cannulation of the compression element 201 provides a predetermined compression level in the compression device 101. In at least one embodiment, the cannulation of the compression element 201 advantageously allows for programmable compression levels without changing a footprint of the compression element (or device overall). For example, without cannulation, providing a first level of compression may require a compression element of a first diameter, while providing a second level of compression may require a compression element of a second diameter. In the same example, the second diameter is greater than the first diameter and, thus, increases a footprint of the compression element. Continuing the example, the increased footprint of the compression element may further require an increase in the footprint of the threaded body 103 or an increase in the cannulation thereof, which may compromise the rigidity of the threaded body 103 and undesirably increase a risk of undesirable bending, or other deformations and failures.

Figure 6:
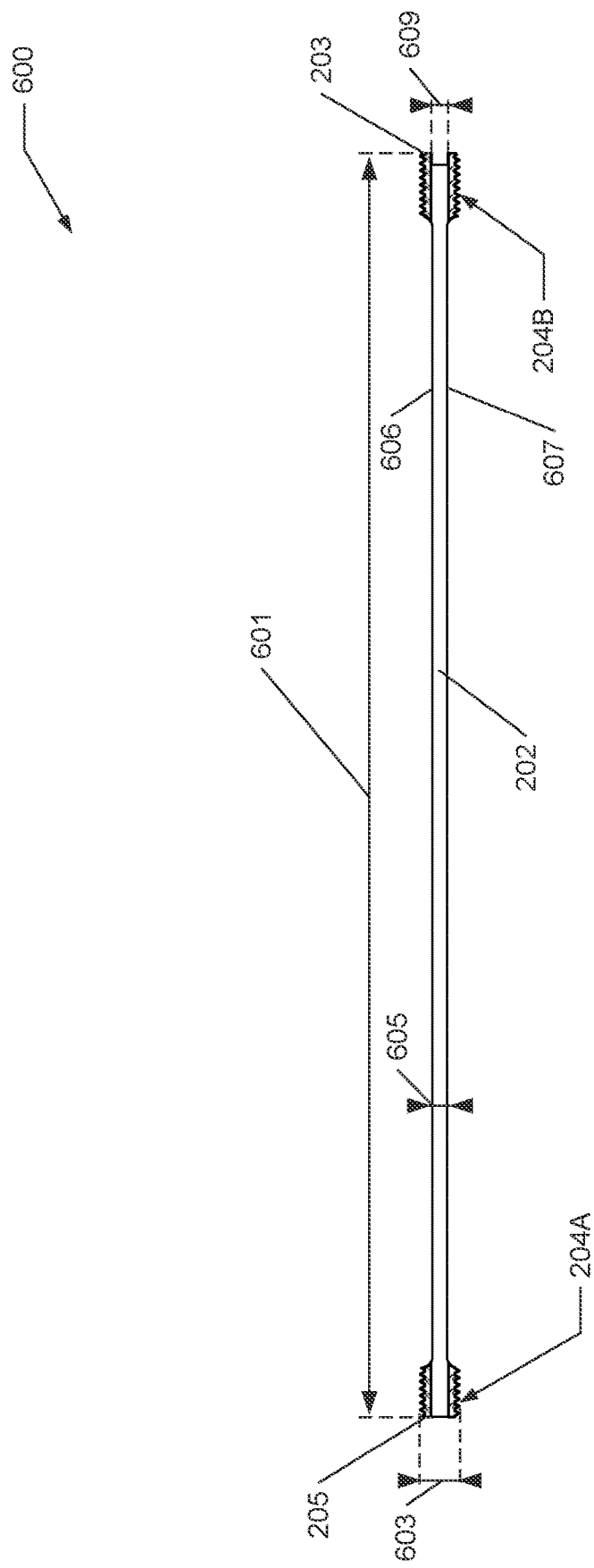
FIG. 6 shows a cross-sectional view of an exemplary compression element according to one embodiment of the present disclosure.

According to one embodiment, a section line 508A, 508B indicates a cross-section 600 of the compression element 201 shown in FIG. 6.

FIG. 6 shows a cross-section 600 of the compression element 201. In various embodiments, the compression element 201 generates compressive loads (e.g., via application of tensile forces) that measure about 50-800 Newtons (N), about 50-100 N, about 100-150 N, about 150-200 N, about 200-250 N, about 250-300 N, about 300-350 N, about 350-400 N, about 400-450 N, about 450-500 N, about 500-550 N, about 550-600 N, about 600-650 N, about 650-700 N, about 700-750 N, about 750-800 N, or about 800-850 N. According to one embodiment, the compression element 201 includes a length 601 between the second end 205 and first end 203. In various embodiments, the length 601 measures about 20-140 mm, about 20-40 mm, about 30 mm, about 40-60 mm, about 60-80 mm, about 80-100 mm, about 100-120 mm, about 120 mm, or about 120-140 mm. In at least one embodiment, the second end 205 and first end 203 include a diameter 603 that measures about 1.0-4.0 mm, about 1.0-1.5 mm, about 1.5-2.0 mm, about 2.0-2.5 mm, about 2.5 mm, about 2.5-3.0 mm, about 3.0-3.5 mm, or about 3.5-4.0 mm. According to one embodiment, the diameter 603 is at least partially determined by a size of the threads 204A, 204B. In at least one embodiment, the threads 204A, 204B are M2.5×0.45 threads.

In one or more embodiments, the shaft 202 includes a thickness 605 between opposing edges 606 and 607. According to one embodiment, the thickness 1105 measures about 0.5-3.0 mm, about 0.5-1.0 mm, about 0.9 mm, about 1.0-1.5 mm, about 1.5-2.0 mm, about 2.0-2.5 mm, or about 2.5-3.0 mm. In at least one embodiment, the compression element 201 includes an internal diameter 609 that measures about 0.25-2.0 mm, about 0.25-0.5 mm, about 0.5-0.75 mm, about 0.75-1.0 mm, about 1.0-1.25 mm, about 1.1 mm, about 1.25-1.5 mm, about 1.5-1.75 mm, or about 1.75-2.0 mm. In various embodiments, the internal diameter 609 refers to the level of cannulation of the compression element 201. According to one embodiment, the internal diameter 609 is such that a guidewire may be inserted through the compression element 201.

Figure 7:
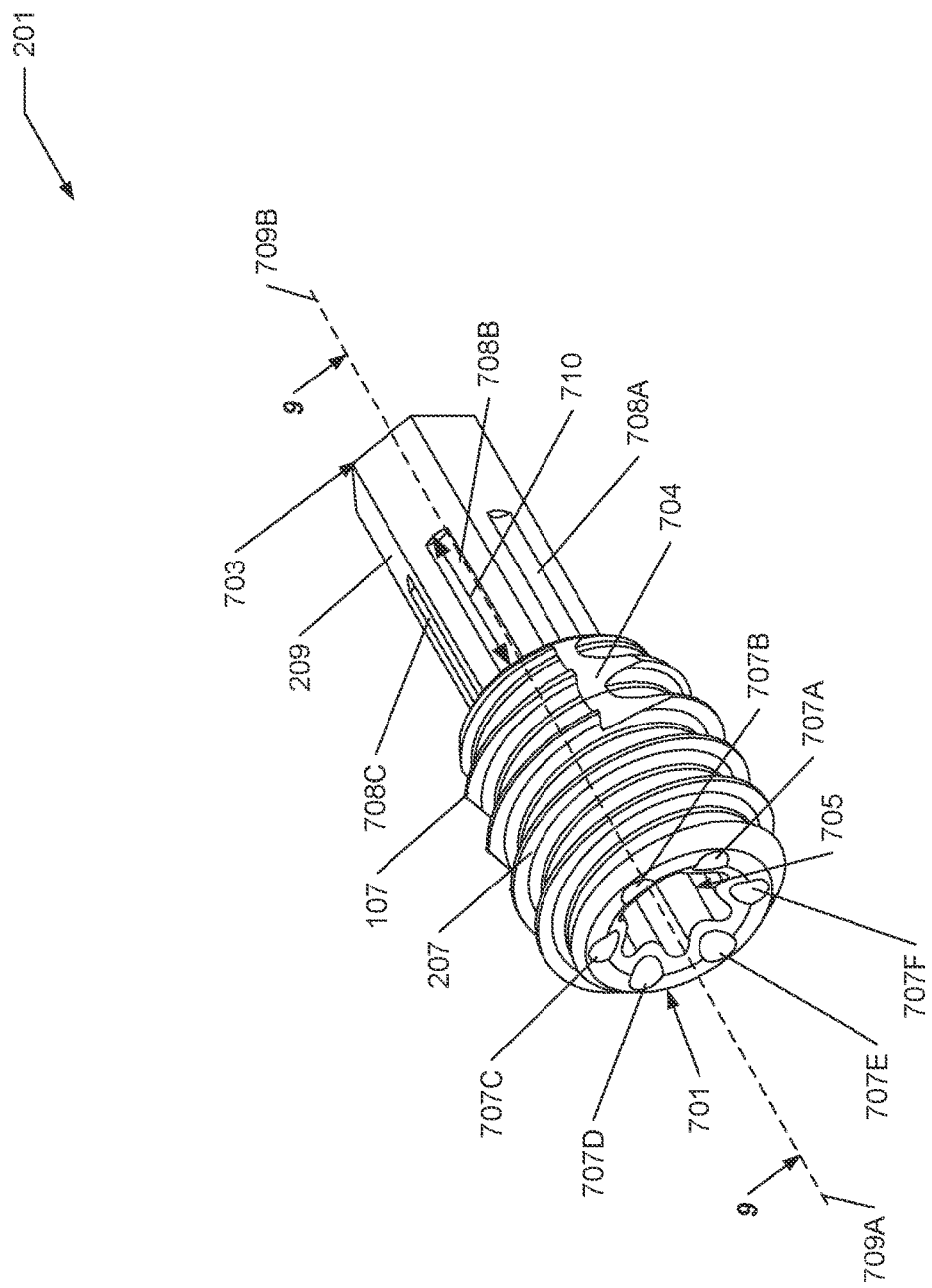
FIG. 7 shows a perspective view of an exemplary sliding element according to one embodiment of the present disclosure.

FIG. 7 shows a perspective view of a sliding element 106. In various embodiments, the sliding element 106 achieves various functions including, but not limited to, temporarily tethering the rotation of an insertion tool and a compression device (e.g., thereby facilitating insertion of the compression device to a target site), enabling a connected threaded body to be pushed away from the sliding element 106 such that a compression element connected therebetween is stretched, and opposing movement of the threaded body toward the sliding element 106 (e.g., thereby maintaining the stretched state of a compression element).

In one or more embodiments, the sliding element 106 includes a first portion 207 toward a first end 701 and a second portion 209 toward a second end 703. In some embodiments, when the compression device 101 is inserted to a target site, the first portion 207 abuts against bone at the target site, thereby applying a compressive force. In various embodiments, the first portion 207 includes a substantially rounded shape, such as, for example, a substantially smooth lag shape (e.g., without threads) that contacts and applies compression to a target site as the compression device 101 is inserted by pressing against an end of a bone, opposed to being drilled into bone via threads (e.g., and further applies compression in response to tensile forces from a connected compression element).

In at least one embodiment, the first portion 207 includes threads 107 for penetrating tissue and securing an implanted position of the compression device 101. In some embodiments, near the first end 701, the first portion 207 includes a substantially rounded and threadless first region followed by a second region that includes threads 107.

In various embodiments, at the first end 701, the first portion 207 forms a void 705 configured for receiving the connection bolt 211 and/or a guidewire. According to one embodiment, the void 705 includes one or more shapes including, but not limited to, hexalobe, circle, square, hexagon, and other polygons. In at least one embodiment, the void 705 is shaped to conform to a footprint of the first end 215 (FIG. 2) of an insertion tool. In some embodiments, the first portion 207 includes one or more flutes 704 that allow the sliding element 106 to self-tap into a target site (e.g., in response to rotation).

In various embodiments, the first portion 207 includes a plurality of voids 707A, 707B, 707C, 707D, 707E, 707F, each configured for receiving a control pin 108 and extending through the first portion 207. In at least one embodiment, the second portion 209 includes a plurality of channels 708A, 708B, 708C, each configured for receiving a control pin 108 inserted through a void 707. According to one embodiment, a length 710 of the channels 708A, 708B, 708C may determine a maximum stretch distance of the compression element 201. For example, an increased length 710 may reduce the maximum stretch distance of the compression element 201. In various embodiments, the length 710 measures about 3.0-9.0 mm, about 3.0-4.0 mm, about 4.0-5.0 mm, about 5.0-6.0 mm, about 6.0-7.0 mm, about 6.18 mm, about 7.0-8.0 mm, or about 8.0-9.0 mm.

In one or more embodiments, upon insertion into the plurality of voids 707A-F, the plurality of control pins 108 allow the compression device 101 (FIG. 1) to be rotated via rotation of the insertion tool 102. In at least one embodiment, the plurality of control pins 108 and voids 707A-F allow for the threaded body 103 to be pushed away from the sliding element 106 via a force applied to the insertion tool 102 (e.g., when the sliding element 106 is secured against movement for the purposes of stretching the compression element 201 of the compression device 101). In one or more embodiments, when the compression element 201 is stretched and a connection bolt 211 is inserted into the insertion device 102, the plurality of control pins 108 maintain a stretched state of the compression element 201 by preventing movement of the threaded body 103 toward the sliding element 106.

In some embodiments, the control pins 108 are omitted and the second end 217 (FIG. 2) conforms to the shape of the opening 705. In one example, the opening 705 receives the second end 217 of the insertion tool 102 to allow for rotation of the compression device 101 via rotation of the insertion tool 102. In the same example, stretching the compression element 201 of the assembled compression device 101 includes securing the threaded body 103 against movement and applying a force to the sliding element 106 such that the sliding element 106 moves away from the threaded body 103, thereby stretching the compression element 201. In an example, stretching the compression element 201 includes securing the sliding element 106 in a stationary position and applying a force to threaded body 103 that causes the threaded body 103 to move away from the sliding element 106, thereby stretching the compression element 201.

In one or more embodiments, the stretched state of the compression element 201 can be maintained by providing a barrier, such as a section of material, between the sliding element 106 and threaded body 103 that prevents movement of the threaded body 103 toward the sliding element 106. In one example, a removable section of material is inserted between the sliding element 106 and threaded body 103 following stretching. In this example, during or after insertion of the compression device 101 to a target site, the section of material is removed, thereby allowing movement between the threaded body 103 and sliding element 106.

Figure 9:
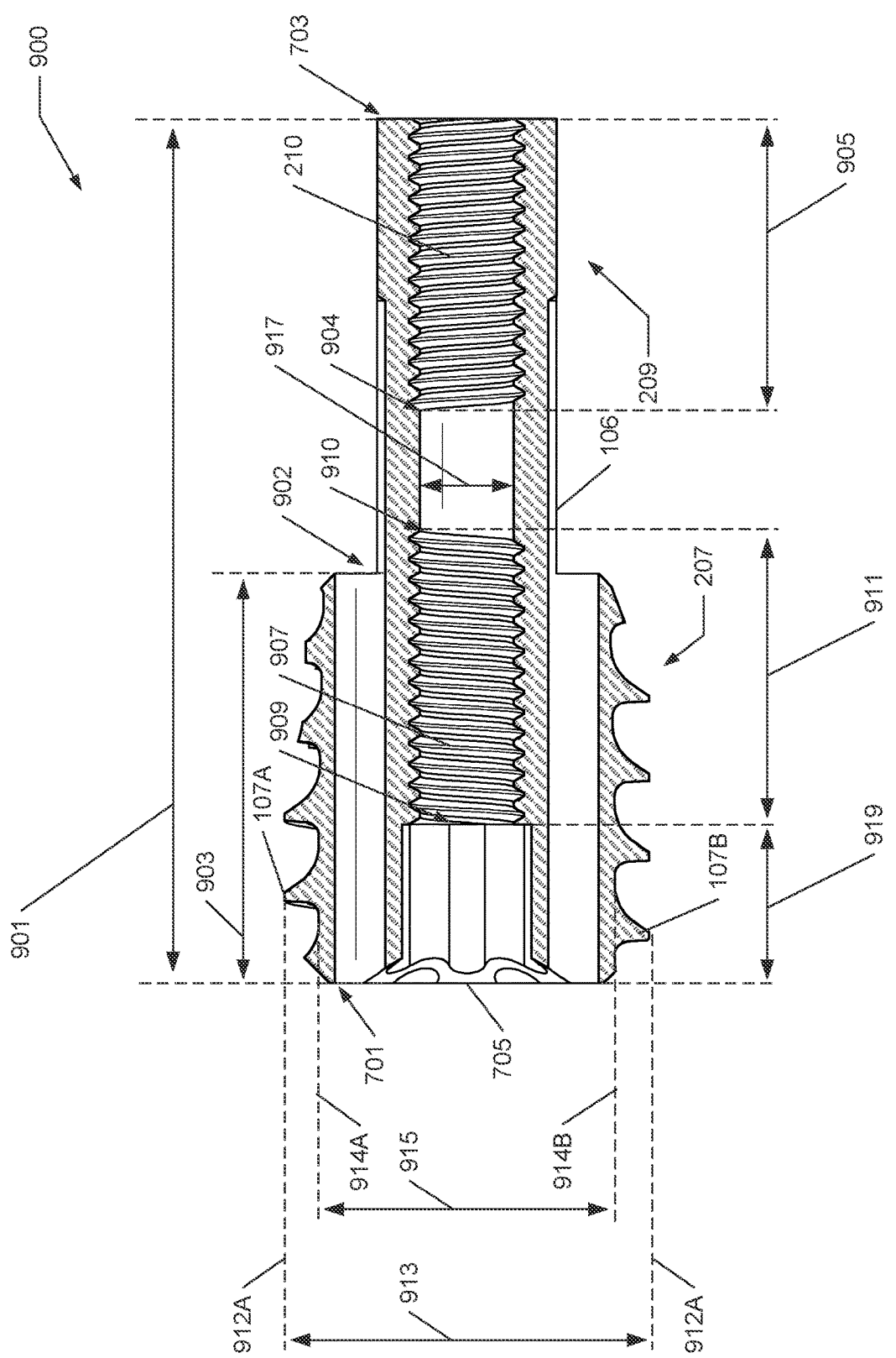
FIG. 9 shows a cross-sectional view of an exemplary sliding element according to one embodiment of the present disclosure.

According to one embodiment, a section line 709A, 709B indicates a cross-section 900 of the sliding element 106 shown in FIG. 9.

Figure 8:
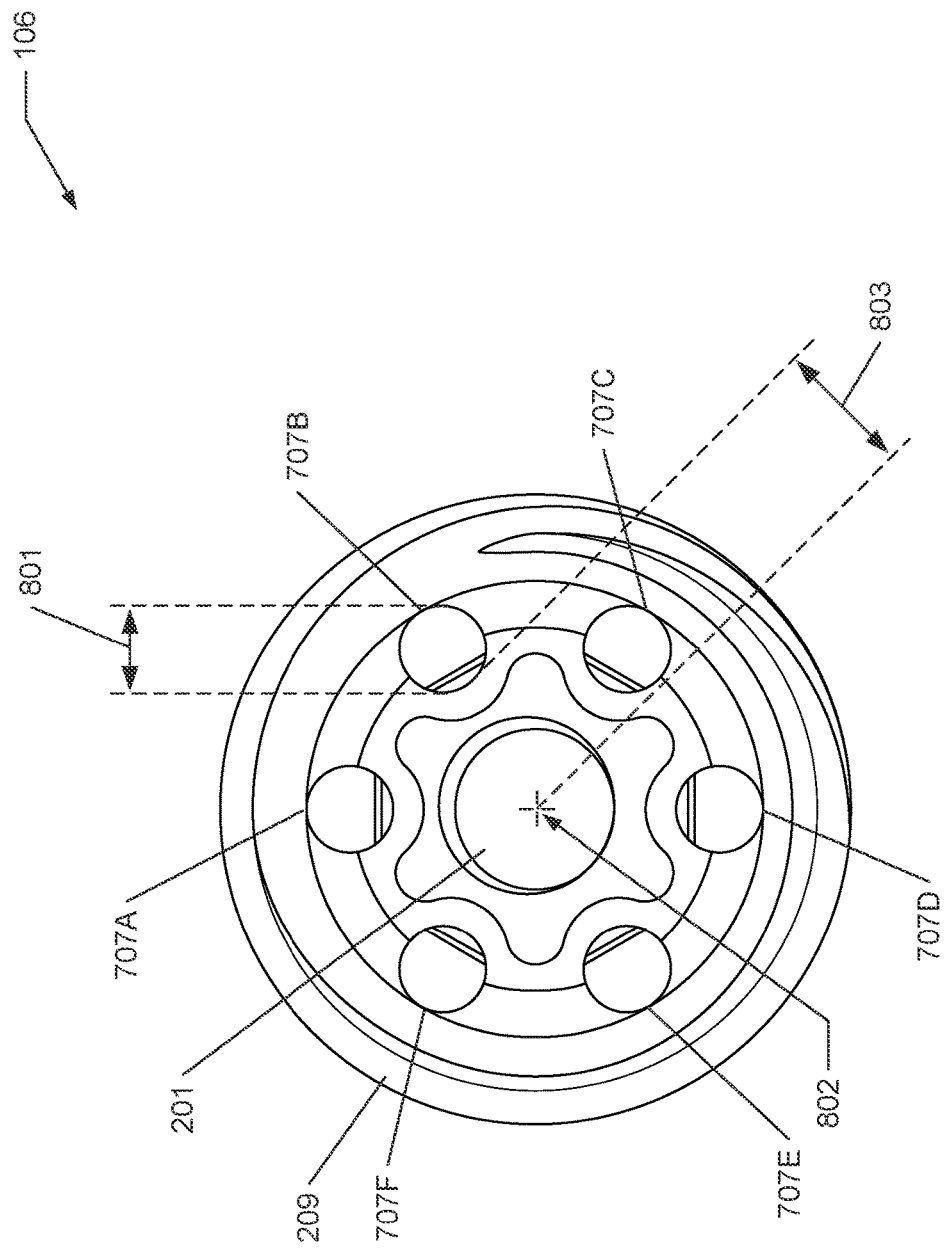
FIG. 8 shows a top view of an exemplary sliding element according to one embodiment of the present disclosure.

FIG. 8 shows a top view of a sliding element 106. In one or more embodiments, the plurality of voids 707A, 707B, 707C, 707D, 707E, 707F each include a diameter 801 that measures about 0.5-3.0 mm, about 0.5-1.0 mm, about 1.0-1.5 mm, about 1.1 mm, about 1.5-2.0 mm, about 2.0-2.5 mm, or about 2.5-3.0 mm. In at least one embodiment, each void 707 is located a distance 803 from a central point 802 of the sliding element 106 (e.g., as measured from a nearest point of the void 707 to the central point 802). According to one embodiment, the distance 803 measures about 2.0-8.0 mm, about 2.0-3.0 mm, about 3.0-4.0 mm, about 3.6 mm, about 4.0-5.0 mm, about 5.0-6.0 mm, about 5.8 mm, about 6.0-7.0, about 6.5 mm, or about 7.0-8.0 mm.

FIG. 9 shows a cross-section 900 of a sliding element 106. In one or more embodiments, the sliding element 106 includes a total length 901 between a first end 701 and second end 703. In at least one embodiment, the total length 901 measures about 10.0-40.0 mm, about 10.0-15.0 mm, about 15.0-20.0 mm, about 19.0 mm, about 20.0-25.0 mm, about 25.0-30.0 mm, about 30.0-35.0, or about 35.0-40.0. In one or more embodiments, the first portion 207 includes a length 903 between the first end 701 and a central region 902. According to one embodiment, the length 903 measures about 6.0-12.0 mm, about 6.0-7.0 mm, about 7.0-8.0 mm, about 8.0-9.0 mm, about 9.0 mm, about 9.0-10.0 mm, about 10.0-11.0 mm, or about 11.0-12.0 mm. In various embodiments, the internal portion 210 includes a length 905 between a region 904 and the second end 703. In one or more embodiments, the length 905 measures about 4.0-9.0 mm, about 4.0-5.0 mm, about 5.0-6.0 mm, about 6.0-7.0 mm, about 6.63 mm, about 7.0-8.0 mm, or about 8.0-9.0.

According to one embodiment, the sliding element 106 includes a first threaded portion 907 that is configured to interface with a connection mechanism 221 and thereby secure the sliding element 106 to a connection bolt 211. In one or more embodiments, the threaded portion 907 includes threading 908 to interface with the threads of the connection mechanism 221. In alternate embodiments, the threaded portion 907 includes one or more non-threaded connection mechanisms, such as, for example, a bayonet fitting. In at least one embodiment, the threaded portion 907 includes a length 911 between a first section 909 and a second section 910. According to one embodiment, the length 911 measures about 2.0-8.0 mm, about 2.0-3.0 mm, about 3.0-4.0 mm, about 4.0-5.0 mm, about 5.0-6.0 mm, about 6.0-7.0, about 6.45 mm, or about 7.0-8.0.

In various embodiments, the first portion 207 includes a first diameter 913 between planes 912A, 912B defined by outer surfaces of threads 107A, 107B. According to one embodiment, the first diameter 913 measures about 6.0-12.0 mm, about 6.0-7.0 mm, about 7.0-8.0 mm, about 8.0-9.0 mm, about 8.0 mm, about 9.0-10.0 mm, about 10.0-11.0, or about 11.0-12.0. In one or more embodiments, the first diameter 913 is based on a desired bore size for inserting the compression device 101 into a target site. In at least one embodiment, the first diameter 913 is substantially similar to the diameter 413 of the tip 109. In at least one embodiment, the threads 107A, 107B the first diameter 913 tapers between the first end 701 and the central region 902.

In one or more embodiments, the first portion 207 includes a second diameter 915 between planes 914A, 914B defined by inner surfaces of the threads 107A, 107B. According to one embodiment, the second diameter 915 measures about 2.0-8.0 mm, about 2.0-3.0 mm, about 3.0-4.0 mm, about 4.0-5.0 mm, about 5.0-6.0 mm, about 6.0-7.0, about 6.5 mm, or about 7.0-8.0. In one or more embodiments, the second diameter 915 provides a particular resistance level to pullout forces experienced by the compression device 101 at a target site. According to one embodiment, the first portion 207 and second portion 209 include a cannulation diameter 917. In at least one embodiment, the cannulation diameter 917 permits passage of connection bolt 211 and a guidewire through the sliding element 106. In one or more embodiments, the cannulation diameter 917 measures about 1.0-4.0 mm, about 1.0-1.5 mm, about 1.5-2.0 mm, about 2.0-2.5 mm, about 2.05 mm, about 2.5-3.0 mm, or about 3.5-4.0 mm.

In at least one embodiment, the void 705 includes a length 919 between the first end 701 and first section 909. According to one embodiment, the length 919 measures about 1.0-4.0 mm, about 1.0-1.5 mm, about 1.5-2.0 mm, about 2.0-2.5 mm, about 2.5 mm, about 2.5-3.0 mm, or about 3.5-4.0 mm.

FIG. 10 shows a cross-section 1000 of an exemplary insertion tool 102. In one or more embodiments, the insertion tool 102 includes a total length 1001 between the second end 217 and the first end 215. In at least one embodiment, the total length 1001 measures about 40-80 mm, about 40-50 mm, about 50-60 mm, about 53.75 mm, about 60-70 mm, or about 70-80 mm. In various embodiments, the insertion tool 102 includes a first portion 1003 between a region 1006 and the first end 215. In one or more embodiments, the first portion 1003 includes a length 1005 that measures about 20-60 mm, about 20-30 mm, about 30-40 mm, about 31.45 mm, about 40-50 mm, or about 50-60 mm. In various embodiments, the first portion 1003 tapers from a first diameter 1007 (toward the region 1006) to a second diameter 1009 (toward the first end 215). According to one embodiment, the first diameter 1007 measures about 9.0-15.0 mm, about 9.0-10.0 mm, about 10.0-11.0 mm, about 11.0-12.0 mm, about 12.5 mm, about 12.0-13.0 mm, about 13.0-14.0, or about 14.0-15.0. In at least one embodiment, the second diameter 1009 measures about 4.0-9.0 mm, about 4.0-5.0 mm, about 5.0-6.0 mm, about 6.0-7.0 mm, about 6.5 mm, about 7.0-8.0 mm, or about 8.0-9.0.

In one or more embodiments, the insertion tool 102 includes a second portion 1010 between the second end 217 and the region 1006. In at least one embodiment, the insertion tool 102 includes a cannulated region 1008 running through both the second portion 1010 and first portion 1003. In one or more embodiments, the cannulated region 1008 includes a diameter 1011 that measures about 1.0-4.0 mm, about 1.0-1.5 mm, about 1.5-2.0 mm, about 2.0-2.5 mm, about 2.6 mm, about 2.5-3.0 mm, or about 3.5-4.0 mm. In various embodiments, the diameter 1011 is such that a portion of a connection bolt 211 may be inserted through the cannulated region 1008. In various embodiments, the diameter 1011 is less than a diameter 1103 of the connection bolt head 223 (FIG. 11), thereby preventing passage of the head 223 through the cannulated region 1008.

In at least one embodiment, the second portion 101 includes an opening 1002 at the second end 217. In one or more embodiments, the opening 1002 is configured for receiving a portion of a connection bolt 221 and for preventing further insertion of the connection bolt 221 by interfacing with the head 223 thereof (FIG. 2). In at least one embodiment, the opening 1002 includes a diameter 1013 that measures about 2.0-8.0 mm, about 2.0-3.0 mm, about 3.0-4.0 mm, about 4.0-5.0 mm, about 5.25 mm, about 5.0-6.0 mm, about 6.0-7.0, or about 7.0-8.0. According to one embodiment, the diameter 1013 conforms to a diameter 1103 of the head 223 (see FIG. 11). In one or more embodiments, the opening 1002 includes a length 1015 that measures about 2.0-6.0 mm, about 2.0-3.0 mm, about 3.0-4.0 mm, about 4.0-5.0 mm, about 4.0 mm, or about 5.0-6.0 mm. According to one embodiment, the length 1015 conforms to a length 1105 of the head 223.

In some embodiments, the insertion tool 102 includes indicia (not shown) and/or a gauge (not shown) for indicating a level of insertion of a compression device into a target site and/or a level of stretch in a compression element. In one example, the insertion tool 102 includes a gauge that records a stretch length of the compression element based on measuring a tensile force applied to a sliding element to which the compression element is connected. In another example, the insertion tool 102 includes a plurality of indicia that are progressively revealed or hidden in response to progressive stretching of the compression element.

FIG. 11 shows a cross-section 1100 of a connection bolt 211. In one or more embodiments, the connection bolt 211 includes a total length 1101 between the first end 218 and the second end 220. In at least one embodiment, the total length 1101 measures about 40-80 mm, about 40-50 mm, about 50-60 mm, about 60.95 mm, about 60-70 mm, or about 70-80 mm. According to one embodiment, the head 223 includes a diameter 1103 that measures about 2.0-6.0 mm, about 2.0-3.0 mm, about 3.0-4.0 mm, about 4.0-5.0 mm, about 4.415 mm, or about 5.0-6.0 mm. According to one embodiment, the diameter 1103 is based on a diameter 1011 of the opening 1002 of the insertion tool 102 (see FIG. 10). In various embodiments, the head 223 includes a length 1105 between the first end 218 and an end 1102 of the head 223. According to one embodiment, the length 1105 measures about 1.0-4.0 mm, about 1.0-1.5 mm, about 1.5-2.0 mm, about 2.0-2.5 mm, about 2.45 mm, about 2.5-3.0 mm, or about 3.5-4.0 mm. In at least one embodiment, the length 1105 is such that the connection bolt 211 is insertable through the insertion tool 102 and into the compression device 101 to a predetermined length.

In one or more embodiments, the connection bolt 211 includes a shaft 1106 between the end 1102 and the second end 220. In at least one embodiment, the shaft 1106 includes a diameter 1107 that measures about 1.0-4.0 mm, about 1.0-1.5 mm, about 1.5-2.0 mm, about 2.0-2.5 mm, about 2.5 mm, about 2.5-3.0 mm, or about 3.5-4.0 mm. In one or more embodiments, the connection bolt 211 includes a cannulated region 1108 between the first end 218 and second end 220. In at least one embodiment, the cannulated region 1108 includes a diameter 1109 that measures about 0.5-3.0 mm, about 0.5-1.0 mm, about 1.0-1.5 mm, about 1.1 mm, about 1.5-2.0 mm, about 2.0-2.5 mm, or about 2.5-3.0 mm. According to one embodiment, the diameter 1109 is such that the connection bolt 102 may be deployed along a guidewire passing through the cannulated region 1108. In various embodiments, the connection mechanism 221 includes a length 1111 between an end 1112 and the second end 220. In one or more embodiments, the length 1111 measures about 2.0-8.0 mm, about 2.0-3.0 mm, about 3.0-4.0 mm, about 4.0-5.0 mm, about 4.5 mm, about 5.0-6.0 mm, about 6.0-7.0, or about 7.0-8.0.

Figure 12:
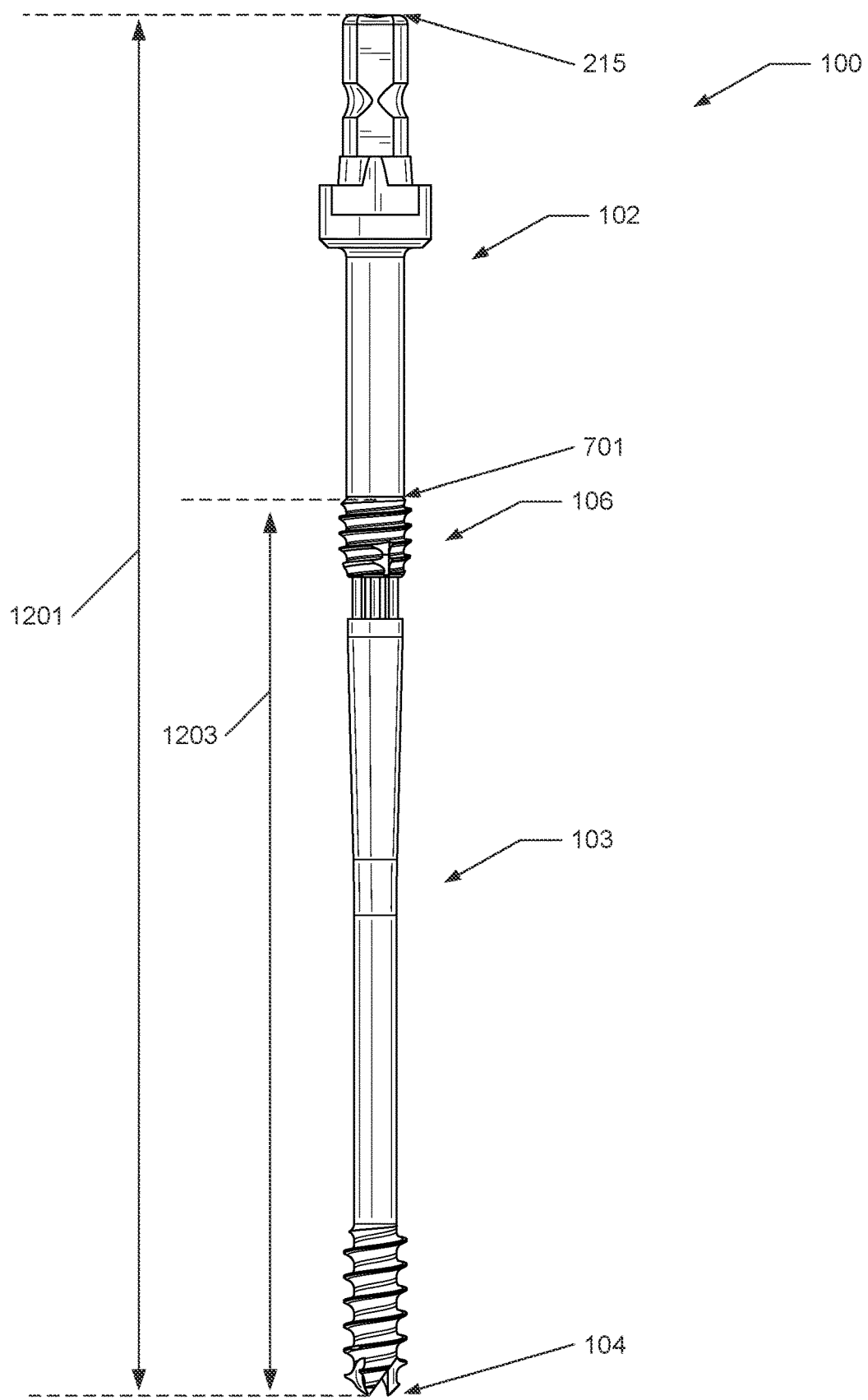
FIG. 12 shows a front view of an exemplary compression assembly according to one embodiment of the present disclosure.

FIG. 12 shows a front view of an exemplary compression assembly 100. In various embodiments, the compression assembly 100 includes a length 1201 between the second end 217 and the first end 104. According to one embodiment, the length 1201 measures about 80-240 mm, about 80-120 mm, about 120-160 mm, about 154.75 mm, about 160-200 mm, or about 200-240 mm. In one or more embodiments, the compression device 101 includes a total length 1203 between the first end 701 and the first end 104. In at least one embodiment, the total length 1203 measures about 80.0-120.0 mm, about 80.0-90.0 mm, about 90.0-100.0 mm, about 100.0-110.0 mm, about 100.5 mm, or about 110.0-120.0 mm. In one or more embodiments, the length 1201 and/or the length 1203 are based on dimensions of a target site, such as, for example, a desired penetration distance of the compression device 101 into the target site.

According to one embodiment, the compression device 101 shown in FIG. 12 is in a pre-stretched state. As shown in FIG. 12, in at least one embodiment, the sliding element 106 has been drawn fully upwards (e.g., held in place via a connection bolt 211, not shown), thereby stretching a compression element 201 (not shown) to a maximum stretch length. In one or more embodiments, upon insertion of the compression device 101 to a target site, the connection bolt 211 may be disconnected from the sliding element 106, thereby transferring a compressive load to the sliding element 106. In one or more embodiments, the compressive load applied to the sliding element 106 by compression element 201 is accompanied by an opposing compressive load applied to the threaded body 103. In at least one embodiment, the opposing compressive loads are transferred to surrounding tissue at the target site. In various embodiments, the compressive loads are sustained as the compression element 201 contracts and attempts to return to an original pre-stretch length.

Figure 13:
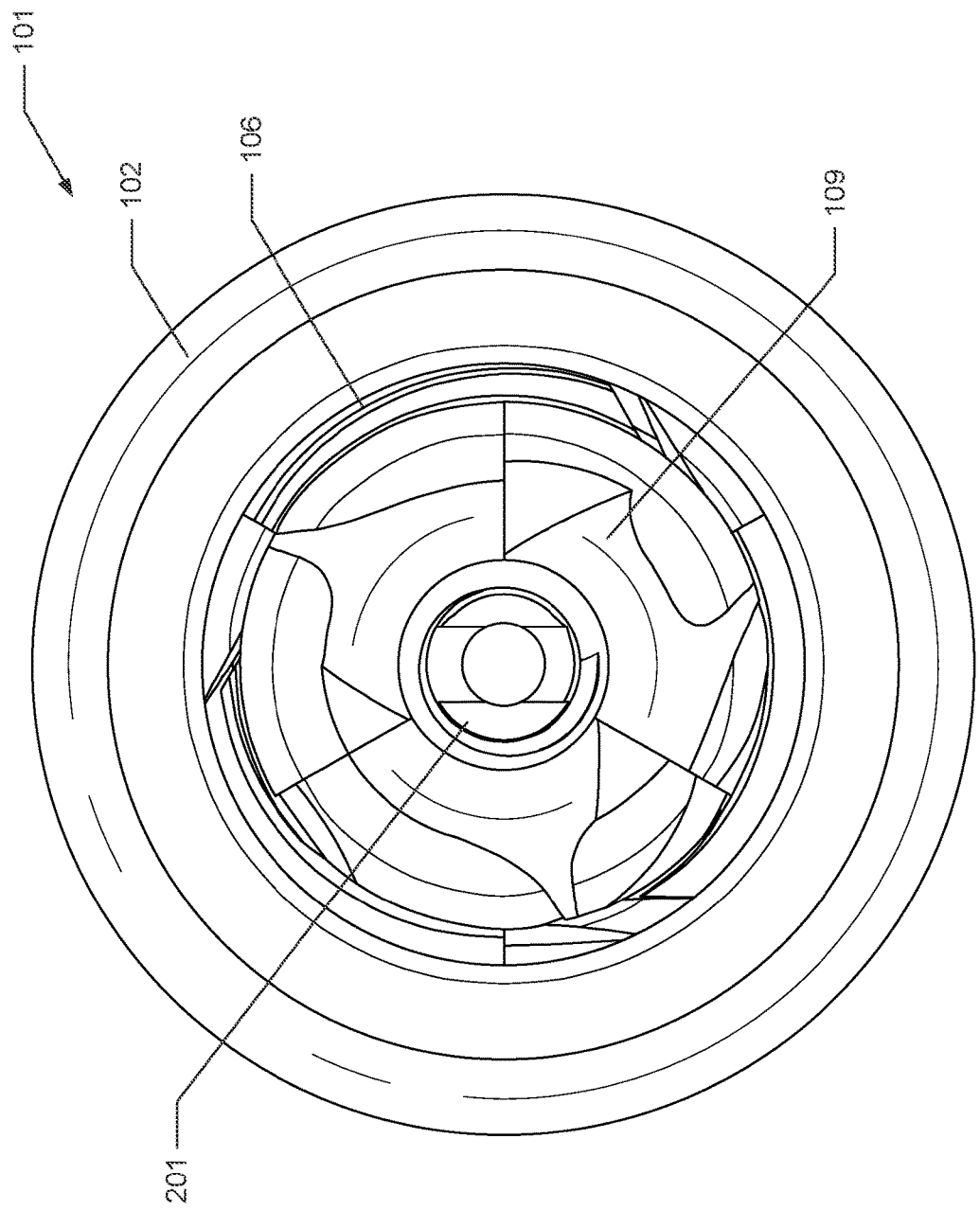
FIG. 13 shows a bottom view of an exemplary compression device according to one embodiment of the present disclosure.

FIG. 13 shows a bottom view of an exemplary compression device 101.

Figure 14:
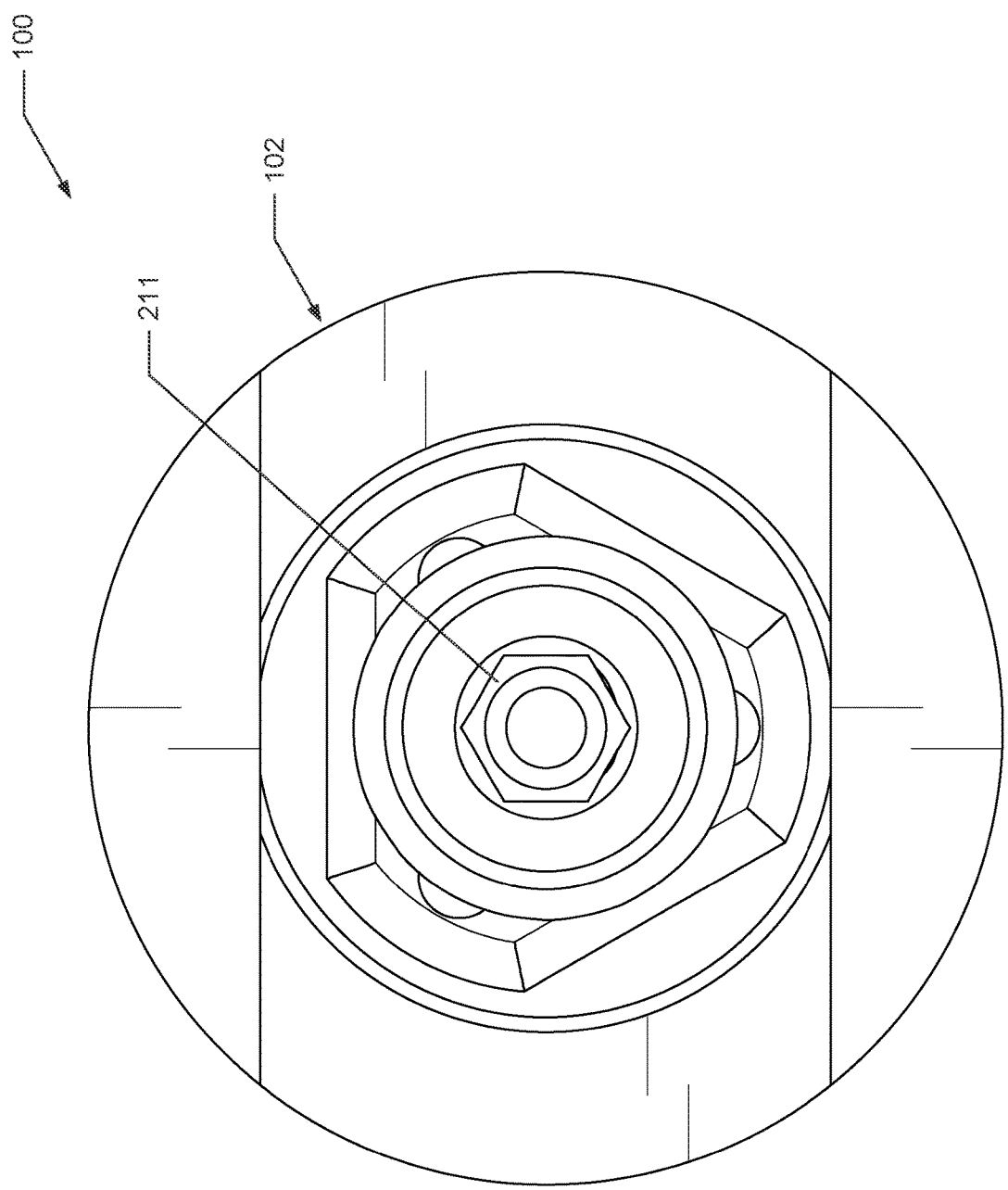
FIG. 14 shows a top view of an exemplary insertion tool and connection bolt according to one embodiment of the present disclosure.

FIG. 14 shows a top view of an exemplary insertion tool 102 and connection bolt 211.

Figure 15:
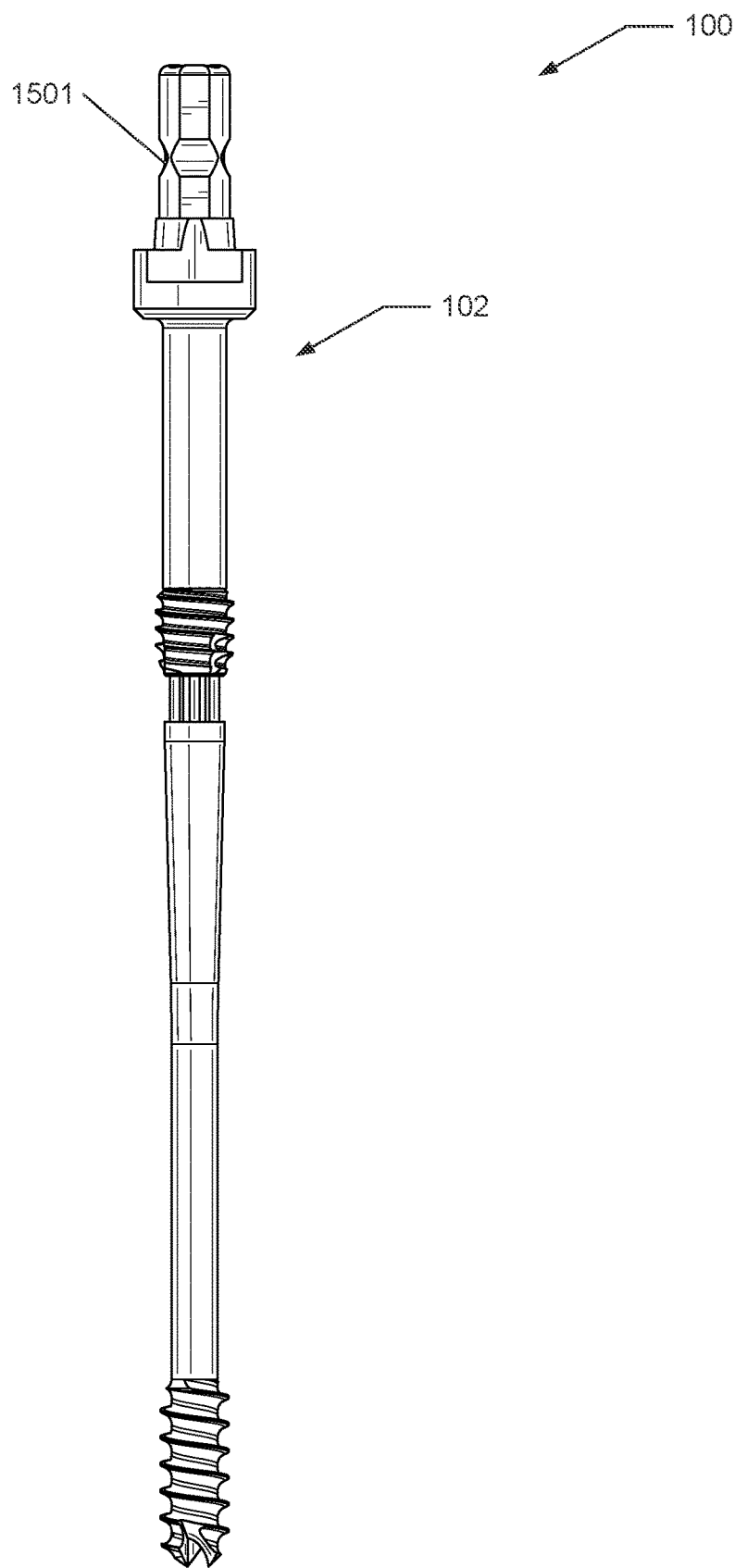
FIG. 15 shows a back view of an exemplary compression assembly according to one embodiment of the present disclosure.

FIG. 15 shows a back view of an exemplary compression assembly 100. In some embodiments, a handle (not shown) is connected to the insertion tool 102 via one or more quick connect features 1501. In at least one embodiment, the insertion tool 102 excludes the quick connect features 1501 and, instead, receives a separate driver (not shown) that includes quick connect features for connection to the handle.

Figure 16:
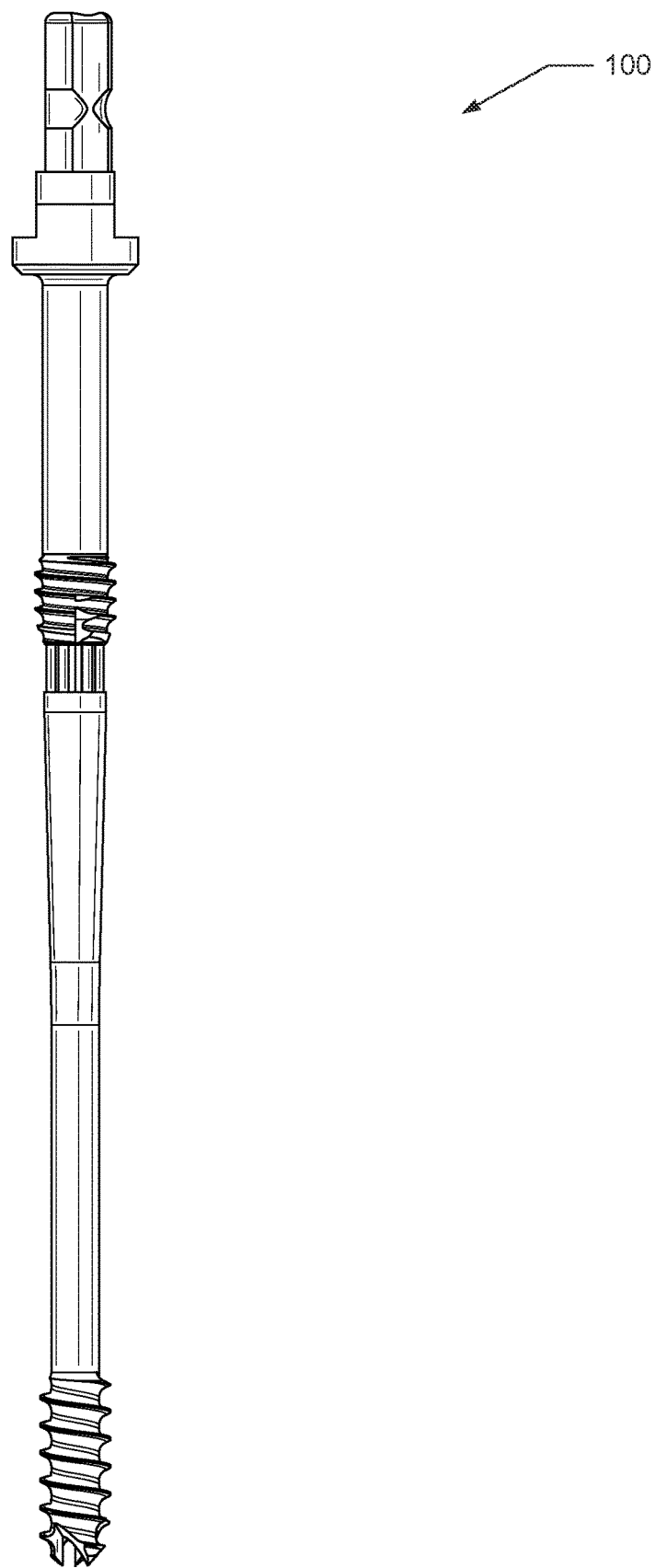
FIG. 16 shows a left-side view of an exemplary compression assembly according to one embodiment of the present disclosure.

FIG. 16 shows a left-side view of an exemplary compression assembly 100.

Figure 17:
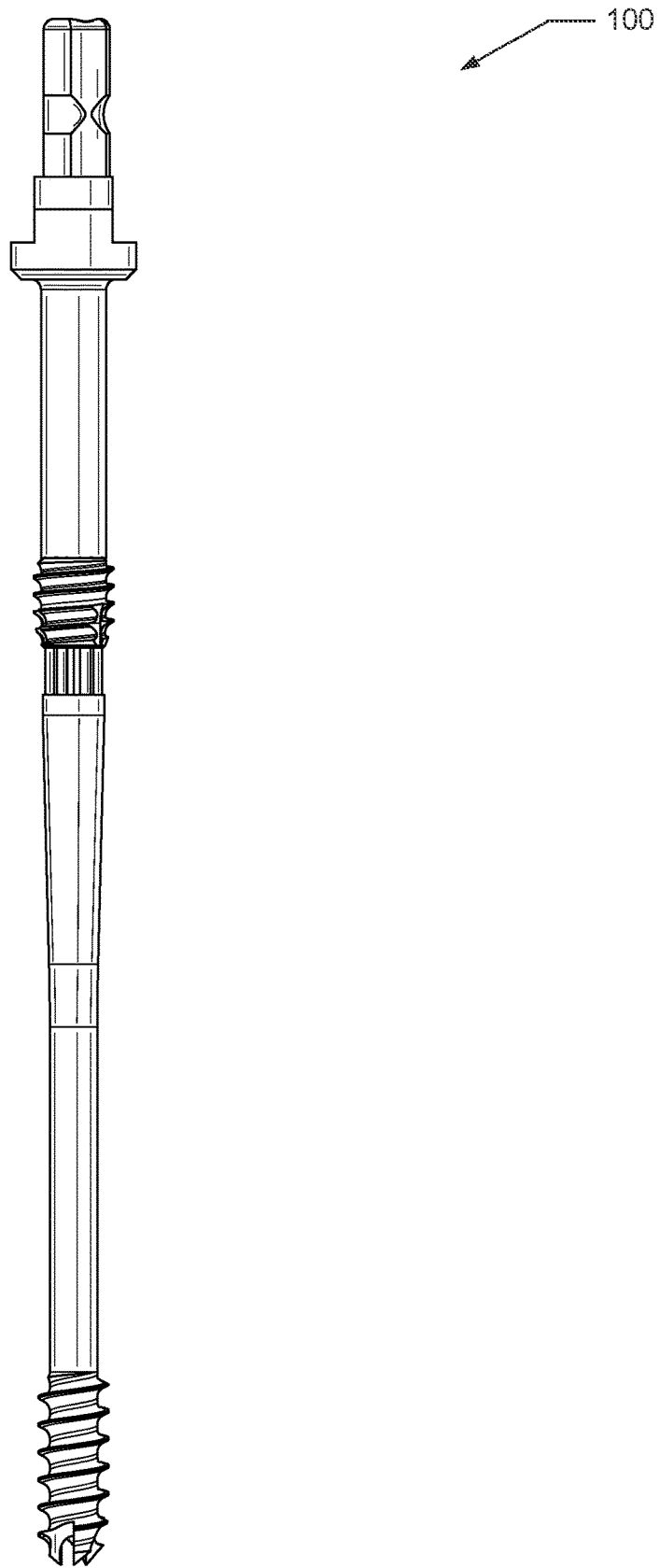
FIG. 17 shows a right-side view of an exemplary compression assembly according to one embodiment of the present disclosure.

FIG. 17 shows a right-side view of an exemplary compression assembly 100.

Figure 18:
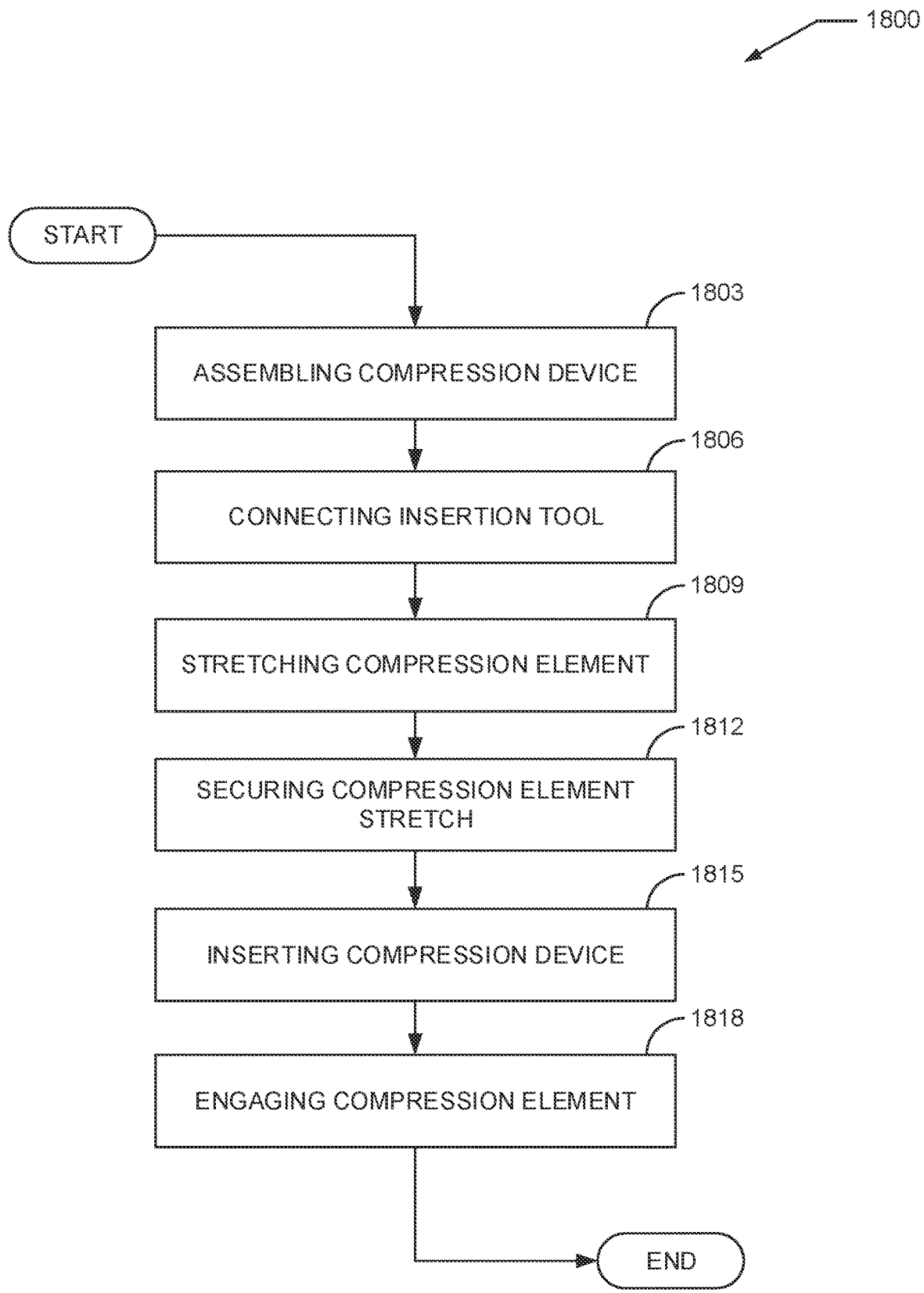
FIG. 18 shows an exemplary compression process, according to one embodiment of the present disclosure.

Before turning to the process flow diagrams of FIG. 18, it is noted that embodiments described herein may be practiced using an alternative order of the steps illustrated in FIG. 18. That is, the process flows illustrated in FIG. 18 are provided as examples only, and the embodiments may be practiced using process flows that differ from those illustrated. Additionally, it is noted that not all steps are required in every embodiment. In other words, one or more of the steps may be omitted or replaced, without departing from the spirit and scope of the embodiments. Further, steps may be performed in different orders, in parallel with one another, or omitted entirely, and/or certain additional steps may be performed without departing from the scope of the embodiments.

FIG. 18 shows an exemplary compression process 1800, according to one embodiment. At step 1803, the process 1800 includes assembling a compression device, such as a compression device 101 (FIG. 1). In at least one embodiment, assembling the compression device includes, but is not limited to, securing opposing ends of a compression element to a sliding element and a threaded body, respectively. In one example, the compression element, sliding element, and/or threaded body are rotated to engaged threaded portions of each component and provide a secure connection. In another example, bayonet or luer-lock style fittings are engaged between each element to assemble to compression device. In some embodiments, the compression element is threaded into the threaded body and sliding element substantially simultaneously.

At step 1806, the process 1800 includes connecting the compression device to an insertion tool, such as an insertion tool 102 (FIG. 1). In various embodiments, connecting the compression device to the insertion tool includes, but is not limited to, inserting a plurality of pins (e.g., pins 108 shown in FIG. 1) through a plurality of voids in the sliding element such that the plurality of pins contact an end of the threaded body (e.g., a second end 105 of the threaded body 103 shown in FIG. 1). In at least one embodiment, the plurality of voids allow the compression device to translate along the plurality of pins (e.g., in response to a force applied at either end of the compression device).

At step 1809, the process 1800 includes stretching the compression element. In at least one embodiment, stretching the compression element includes securing a stationary position of the sliding element while applying a force to an end of the threaded body, thereby causing the threaded body to translate away from the sliding element and resulting in the stretching of the compression element. In one example, the compression device and attached insertion tool are placed into a stretching device. In this example, a locking mechanism secures the stationary position of the sliding element by creating a threaded connection between the locking mechanism and external threads of the sliding element. Continuing the example, after the sliding element is secured, a pushing mechanism applies a force to the insertion tool, and the plurality of pins of the insertion tool translate the applied force to the end of the threaded body. In the same example, the force causes the insertion tool to translate toward the sliding element and causes the threaded body to translate away from the sliding element, thereby stretching the compression element. In some embodiments, the compression element is stretched until an end of the insertion tool contacts an end of the sliding element. In at least one embodiment, the compression element is stretched until a predetermined length of the plurality of pins translates through the sliding element.

In some embodiments, stretching of the compression element occurs during insertion of the compression device to a target site. In one example, rotation of a compression device into a target site causes the compression element to progressively stretch. In this example, the compression device is rotated into the target site until a predetermined level of stretch is achieved in the compression element.

At step 1812, the process 1800 includes securing the stretched position of the compression element. According to one embodiment, the stretched position is secured while the compression device and insertion tool are disposed within a stretching device. In at least one embodiment, securing the stretch of the compression element includes inserting a connection bolt through the insertion tool and into the sliding element, and securely attaching the connection bolt to the sliding element (e.g., in an impermanent manner such that the connection bolt may be detached via a tool). In one example, the connection bolt rotates into the sliding element such that corresponding threads on each component are engaged. In another example, rotating the inserted connection bolt engages a bayonet or luer-lock style fitting. In at least one embodiment, the connection bolt is inserted into the sliding element such that an end of the connection bolt contacts an end of the insertion tool (e.g., or surfaces of an opening located at the same), thereby preventing further insertion of the connection bolt. In various embodiments, upon release of the sliding element from the secured position within the stretching device, the compression bolt prevents movement of the insertion tool, thereby preventing contraction of the compression element and preserving the stretched state of the same. In other words, the inserted connection bolt opposes a tensile force applied by the compression element to the sliding element.

In some embodiments, steps 1803-1812 are performed as a first process at a first location (e.g., by a fabrication or assembly entity) and steps 1815-1818 are performed as a second process at a second location (e.g., by a surgeon or technician). In one example, a process for manufacturing a compression device includes steps 1803-1812 and a process for using the compression device includes steps 1815-1818.

At step 1815, the process 1800 includes inserting the compression device into a target site including at least a first and a second bony fragment to be compressed for the purposes of promoting healing. In one example, a surgeon rotates the compression device (e.g., via manual or motorized rotation of the insertion tool) into a target site such that external threading of the sliding element lies in a first bony fragment and external threading of the threaded body lies in a second bony fragment. As will be understood from discussions herein, the sliding element may contact a bony fragment (or other tissue) in any suitable way. In one embodiment, the sliding element includes one or more external threads, such that the sliding element contacts a bony fragment via the one or more external threads drilling into or otherwise engaging with the bony fragment. In some embodiments, the sliding element may include a head (or other feature) such that a portion of the sliding element contacts a surface of a bony fragment (e.g., opposed to drilling into a bony fragment).

At step 1818, the process 1800 includes engaging the compression element such that a compressive force is generated between the first bony fragment and the second bony fragment. In one example, a surgeon disconnects the connection bolt from the sliding element, thereby causing the sliding element to attempt to translate toward the compression element (e.g., in response to the tensile force applied thereby). In the same example, in response to tensile forces from the compression element, the sliding element applies a first sustained compressive force to the first bony fragment and the threaded body applies a second sustained compressive force to the second bony fragment (e.g., the first and second forces being applied in opposing directions). Continuing the example, the compressive forces promote ossification and resettling between the first and second bony fragments. In this example, whereas previous compression solutions may lose compressive force overtime due to resettling and resorption of the bony fragments, the compression element of the present compression device dynamically responds to movement and structural changes at the target site to maintain substantially continuous and constant compression of the first and second bony fragments.

While various aspects have been described in the context of a preferred embodiment, additional aspects, features, and methodologies of the claimed assemblies, devices, and processes will be readily discernible from the description herein, by those of ordinary skill in the art. Many embodiments and adaptations of the disclosure and claimed assemblies, devices, and processes other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed assemblies, devices, and processes. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed assemblies, devices, and processes. In addition, some steps may be carried out simultaneously, contemporaneously, or in synchronization with other steps.

The embodiments were chosen and described in order to explain the principles of the claimed assemblies, devices, and processes and their practical application so as to enable others skilled in the art to utilize the assemblies, devices, and processes and various embodiments and with various modifications as are suited to the particular use contemplated. Alternative embodiments will become apparent to those skilled in the art to which the claimed assemblies, devices, and processes pertain without departing from their spirit and scope. Accordingly, the scope of the claimed assemblies, devices, and processes is defined by the appended claims rather than the foregoing description and the exemplary embodiments described therein.

What is claimed is:

1. A method comprising:
   inserting a compression device assembly into a patient, wherein the compression device assembly comprises:
     an insertion tool defining a hollow interior and comprising one or more pins;
     an elongate threaded body comprising:
       a threaded body first end defining a hollow interior of the threaded body; and
       a threaded body second end comprising an opening to the hollow interior of the threaded body;
     a sliding element defining a hollow interior and comprising:
       a sliding element first end comprising an elongated portion shaped to interface with the opening of the threaded body second end; and
       one or more pin openings receiving for the one or more pins; and
     a nitinol compression element operatively connected to the threaded body and the sliding element;
   contacting the threaded body with a first bony fragment of the patient via one or more threaded body threads;
   contacting the sliding element with a second bony fragment of the patient; and
   applying compression to the first bony fragment and the second bony fragment via the compression element returning to a relaxed state from a deformed state.

2. The method of claim 1, wherein:
   the compression element is cannulated;
   a guidewire is further received through the cannulated compression element; and
   the method further comprises guiding the compression device assembly along the guidewire to a particular location in the patient.

3. The method of claim 1, wherein the compression element is in the deformed state prior inserting the compression device assembly into the patient.

4. The method of claim 1, wherein the compression element is in the relaxed state prior to inserting the compression device assembly into the patient.

5. The method of claim 1, wherein:
   the compression element comprises a compression element elongated portion between a compression element first end and a compression element second end; and
   the compression element first end and the compression element second end each comprise a sloped region for transitioning to the compression element elongated portion.

6. The method of claim 1, wherein:
   the sliding element comprises one or more sliding element threads; and
   a diameter of the one or more threaded body threads is less than a diameter of the one or more sliding element threads.

7. The method of claim 1, wherein the threaded body comprises a wall thickness of 0.5-4.0 mm.

* * * * *